United States Patent
Mitchell et al.

(10) Patent No.: US 8,641,762 B2
(45) Date of Patent: Feb. 4, 2014

(54) SYSTEMS AND METHODS FOR IN SITU ASSEMBLY OF AN INTERSPINOUS PROCESS DISTRACTION IMPLANT

(75) Inventors: Steven T. Mitchell, Pleasant Hill, CA (US); Charles J. Winslow, Walnut Creek, CA (US); Scott A. Yerby, Montara, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 19 days.

(21) Appl. No.: 13/346,332

(22) Filed: Jan. 9, 2012

(65) Prior Publication Data
US 2012/0109205 A1 May 3, 2012

Related U.S. Application Data

(62) Division of application No. 11/874,853, filed on Oct. 18, 2007, now Pat. No. 8,097,019.

(60) Provisional application No. 60/853,963, filed on Oct. 24, 2006.

(51) Int. Cl.
*A61F 2/44* (2006.01)

(52) U.S. Cl.
USPC ........................ 623/17.11; 606/246

(58) Field of Classification Search
USPC .................. 606/246–249, 86 A, 90, 99, 105; 623/17.11–17.16
See application file for complete search history.

(56) References Cited

U.S. PATENT DOCUMENTS

| | | | |
|---|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

"Dispositivo Intervertebrale Ammortizzante DIAM," date unknown, p. 1.

(Continued)

*Primary Examiner* — Mary Hoffman
*Assistant Examiner* — Tara Carter

(57) ABSTRACT

An implant system for implantation between adjacent spinous processes for the relief of pain associated with the spine. The implant has a series of spacers which may be inserted over a shaft located between adjacent spinous processes thus allowing the implant to be assembled in situ. The spacers may rotate on the shaft relative to the wings. To minimize trauma to the patient, each spacer has a tapered tissue expander to distract the opening between the spinous processes during assembly. The shaft is connected to a wing, and a second wing or deployable wing may be inserted over the shaft and locked into place.

17 Claims, 12 Drawing Sheets

(56) References Cited

U.S. PATENT DOCUMENTS

| | | | |
|---|---|---|---|
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,035,712 A | 7/1991 | Hoffman |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove et al. |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,540,689 A | 7/1996 | Sanders et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,391 A | 12/1997 | Lin |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,749,916 A | 5/1998 | Richelsoph |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,436,140 B1 | 8/2002 | Liu et al. |
| 6,440,169 B1 | 8/2002 | Elberg et al. |
| 6,447,513 B1 | 9/2002 | Griggs |
| 6,447,546 B1 | 9/2002 | Bramlet et al. |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,527,803 B1 | 3/2003 | Crozet et al. |
| 6,554,833 B2 | 4/2003 | Levy |
| 6,572,653 B1 | 6/2003 | Simonson |
| 6,582,433 B2 | 6/2003 | Yun |
| 6,582,467 B1 | 6/2003 | Teitelbaum et al. |

(56) References Cited

U.S. PATENT DOCUMENTS

| | | |
|---|---|---|
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,641,673 B2 | 1/2010 | Le Couedic et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 7,927,354 B2 | 4/2011 | Edidin et al. |
| 2001/0016743 A1 | 8/2001 | Zucherman et al. |
| 2001/0049527 A1 | 12/2001 | Cragg |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1* | 4/2003 | Zucherman et al. ............ 606/61 |
| 2003/0153915 A1 | 8/2003 | Nekozuka et al. |
| 2003/0176925 A1 | 9/2003 | Paponneau |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0265074 A1 | 11/2006 | Krishna et al. |
| 2006/0271044 A1 | 11/2006 | Petrini et al. |
| 2006/0271049 A1 | 11/2006 | Zucherman et al. |
| 2006/0271061 A1 | 11/2006 | Beyer et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |

(56) References Cited

U.S. PATENT DOCUMENTS

| | | |
|---|---|---|
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0225810 A1 | 9/2007 | Colleran et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233084 A1 | 10/2007 | Betz et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0177306 A1 | 7/2008 | Lamborne et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0243250 A1 | 10/2008 | Seifert et al. |
| 2008/0262617 A1 | 10/2008 | Froehlich et al. |
| 2008/0281359 A1 | 11/2008 | Abdou |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0099610 A1 | 4/2009 | Johnson et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0264927 A1 | 10/2009 | Ginsberg et al. |
| 2009/0270918 A1 | 10/2009 | Attia et al. |
| 2009/0292316 A1 | 11/2009 | Hess |
| 2009/0326538 A1 | 12/2009 | Sennett et al. |
| 2010/0036419 A1 | 2/2010 | Patel et al. |
| 2010/0121379 A1 | 5/2010 | Edmond |
| 2010/0191241 A1 | 7/2010 | McCormack et al. |
| 2010/0204732 A1 | 8/2010 | Aschmann et al. |
| 2010/0211101 A1 | 8/2010 | Blackwell et al. |
| 2011/0054531 A1 | 3/2011 | Lamborne et al. |
| 2011/0144692 A1 | 6/2011 | Saladin et al. |
| 2011/0166600 A1 | 7/2011 | Lamborne et al. |

FOREIGN PATENT DOCUMENTS

| | | |
|---|---|---|
| DE | 4012622 C1 | 7/1991 |
| DE | 202006018978 U1 | 2/2007 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2003 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Discord Tech., 2006, vol. 00, No. 00, pp. 1-7.

Benzel et al., "Posterior Cervical Interspinous Compression Wiring and Fusion for Mid to Low Cervical Spinal Injuries," J. Neurosurg., Jun. 1989, pp. 893-899, vol. 70.

Bini et al., "Minimally Invasive Treatment of Moderate Lumbar Spinal Stenosis with the Superion® Interspinous Spacer," The Open Orthopaedics Journal, May 27, 2011, pp. 361-367, vol. 5.

Buric et al., "DIAM Device for Low Back Pain in Degenerative Disc Disease 24 Months Follow-up," Advances in Minimally Invasive

(56) References Cited

OTHER PUBLICATIONS

Surgery and Therapy for Spine and Nerves, Alexandre et al., eds., 2011, pp. 177-182, Spinger-Verlat/Wien.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, Dispositif Intervertébral Amortissant, Jun. 1998, pp. 1-4.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Kramer et al., "Intervetertebral Disk Diseases: Causes, Diagnosis, Treatment and Prophylaxis," pp. 244-249, Medical, 1990.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Phillips et al., "Biomechanics of Posterior Dynamic Stabiling Device (DIAM) After Facetectomy and Disectomy," The Spine Journal, 2006, vol. 6, pp. 714-722.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," SPINE, 2005, pp. 744-749, vol. 30, No. 7.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," SPINE, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthrodèse," La Revue de Medécine Orthopédique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.
Senegas, "Mechanical Supplementation by Non-Rigid Fixation in Degenerative Intervertebral Lumbar Segments: the Wallis System," Eur. Spine J., 2002, p. 5164-5169, vol. 11, Suppl. 2.
Senegas, "Rencontre," Maîtrise Orthopédique, May 1995, pp. 1-3, No. 44.
Serhan, "Spinal Implants: Past, Present, and Future," 19th International IEEE/EMBS Conference, Oct. 30-Nov. 2, 1997, pp. 2636-2639, Chicago, Illinois.
Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.
Taylor et al., "Analyse d'une experience clinique d'un implant postérieur amortissant," Rachis Revue de Pathologie Vertébrale, Oct./Nov. 1999, vol. 11, No. 4-5, Gieda Inter Rachis.
Taylor et al., "Device for Intervertebral Assisted Motion: Technique and Intial Results," 22 Neurosurg. Focus, Jan. 2007, vol. 22, No. 1, pp. 1-6.
Taylor et al., "Technical and Anatomical Considerations for the Placement of a Posterior Interspinous Stabilizer," 2004, pp. 1-10, Medtronic Sofamor Danek USA, Inc., Memphis, Tennessee.
Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.
Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.
Taylor, "Présentation à un an d'un dispositif amortissant d'assistance discale," 5èmes journées Avances & Controverses en pathologie rachidienne, Oct. 1-2, 1998, Faculté Libre de Médecine de Lille.
Tsuji et al., "Ceramic Interspinous Block (CISB) Assisted Anterior Interbody Fusion," J. Spinal Disorders, 1990, pp. 77-86, vol. 3, No. 1.

(56) References Cited

OTHER PUBLICATIONS

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zhao et al., "Efficacy of The Dynamic Interspinous Assisted Motion System in Clinical Treatment of Degenerative Lumbar Disease," Chin. Med. J., 2010, vol. 123, No. 21, pp. 2974-2977.

Zucherman et al., "Clinical Efficacy of Spinal Instrumentation in Lumbar Degenerative Disc Disease," SPINE, Jul. 1992, pp. 834-837, vol. 17, No. 7.

\* cited by examiner

FIG. 1A
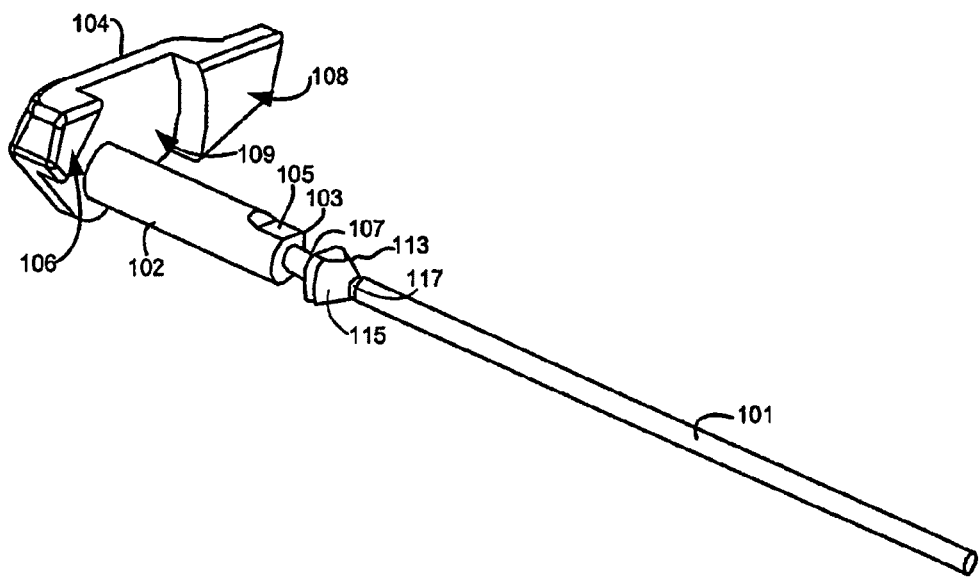
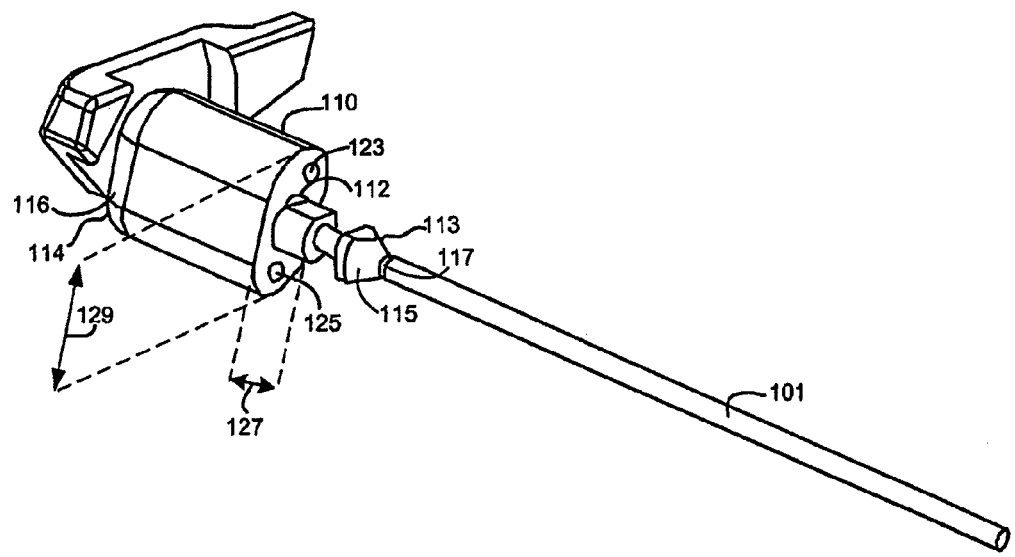
FIG. 1B

FIG. 1C
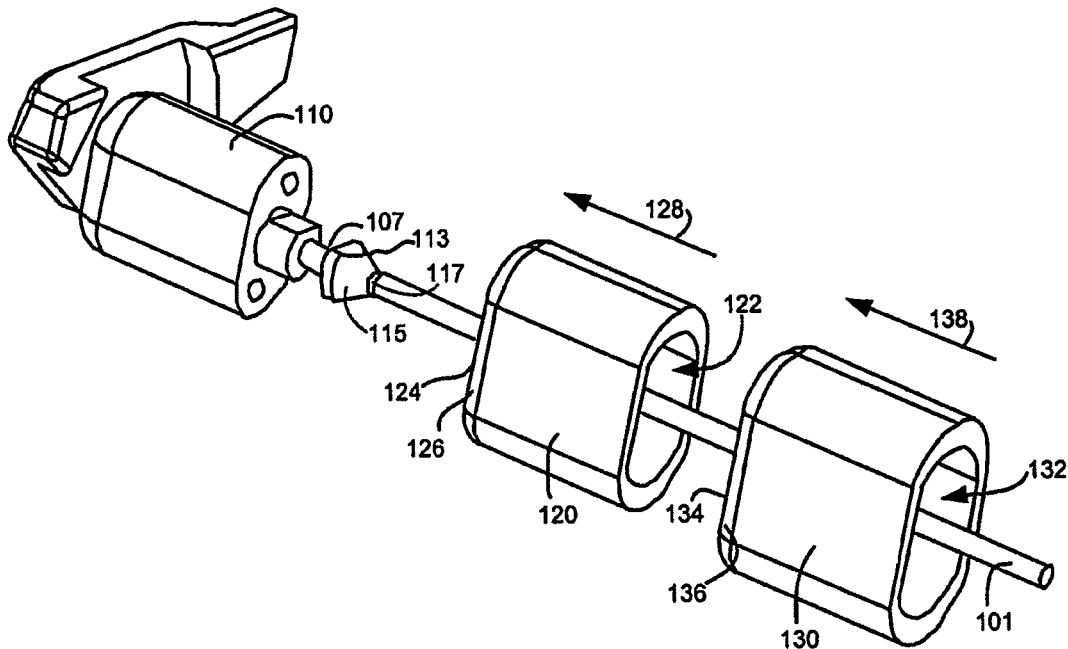
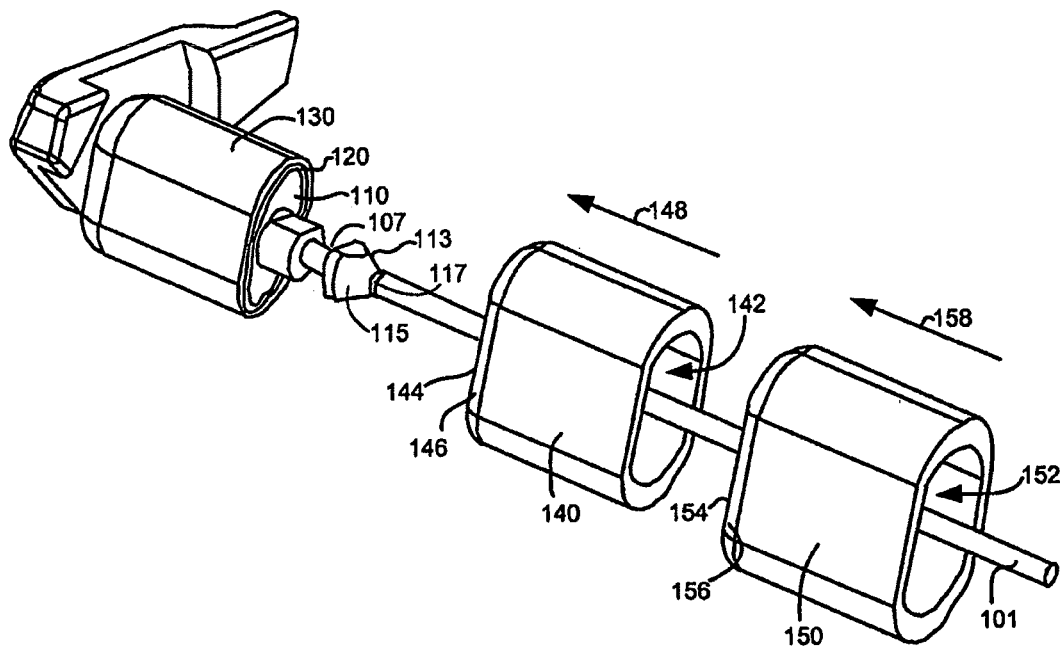
FIG. 1D

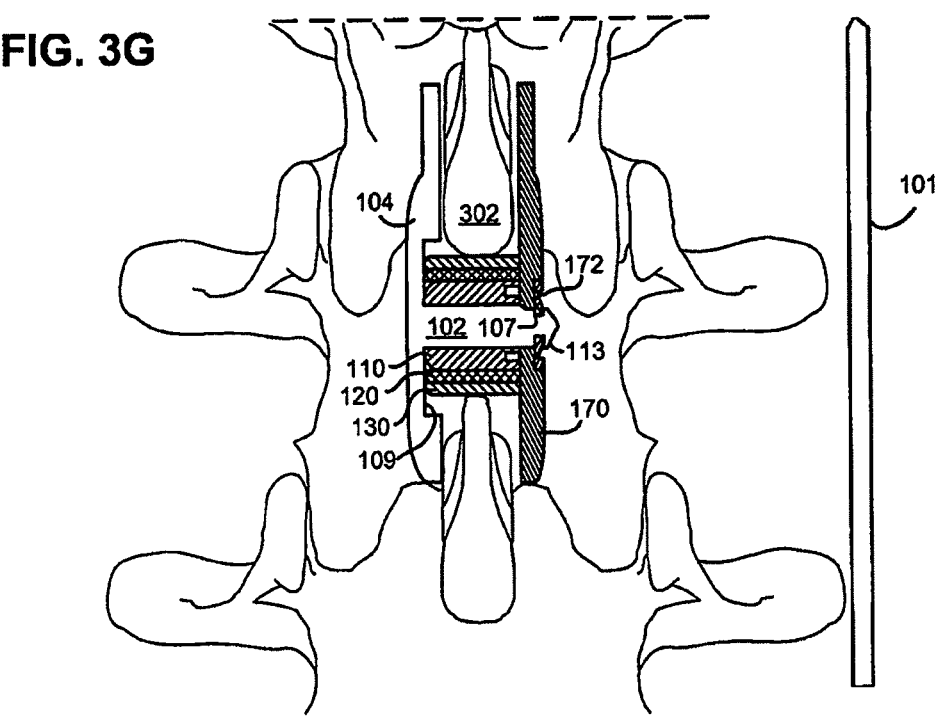

SYSTEMS AND METHODS FOR IN SITU ASSEMBLY OF AN INTERSPINOUS PROCESS DISTRACTION IMPLANT

This application is a divisional of prior application Ser. No. 11/874,853, filed Oct. 18, 2007, and claims the benefit of U.S. Provisional Patent Application No. 60/853,963, filed Oct. 24, 2006, both of which are incorporated herein by reference.

BACKGROUND

The spinal column has many functions including supporting the body, weight transfer, motion, and protection of the spinal cord and the nerve roots The spinal column is a structure composed primarily of bones, ligaments, muscles, and cartilage. The bones of the spinal column are called vertebrae.

As the population ages, it is anticipated that there will be an increase in adverse spinal conditions which are characteristic of weakened bone. Also, with aging come increases in spinal stenosis, which is characterized by thickening of the bones, which make up the spinal column and facet arthropathy. These degenerative conditions as well as physical trauma can lead to failure or instability of the spinal column. Spinal stenosis is characterized by a reduction in the available space for the passage of blood vessels and nerves.

Spinal stenosis in the neck results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space*, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., *Effect of cervical spine motion on the neuroforaminal dimensions of human cervical spine*, Spine, vol. 17 at 1131 (Nov. 10, 1992). In contrast, neck flexion increases the foraminal area. Humpreys, S. C. et al., at 1105. Pain associated with stenosis can be relieved by medication and/or surgery. Accordingly, there have been developed surgical procedures and implants for alleviating conditions such as spinal stenosis, vertebral fracture and other spinal injury.

Placement of spinal implants requires surgery. Open surgery for placement of spinal implants requires a lengthy hospital stay and an extended convalescence. Open surgery also carries increased risk of infection and other complications. Of course, it is desirable to eliminate the need for major surgery for all individuals and in particular for the elderly. Accordingly, there is a need to develop procedures and implants for alleviating degenerative conditions of the spine which are minimally-invasive, can be tolerated by the elderly and can be performed preferably on an outpatient basis.

Minimally-invasive procedures typically access the site of the spinal intervention through small incisions. Minimally-invasive procedures reduce trauma to the tissue thereby reducing hospital and convalescence time and reducing the risk of complications. However, many implants for minimally-invasive spinal interventions must be assembled prior to insertion, thus requiring larger incisions for insertion. Also, once assembled, the size of the implant cannot be changed inside the patient. If a larger implant is required, the smaller implant must first be removed and a new larger implant inserted.

In view of the foregoing background, it would therefore be desirable to have a spinal implant that could be assembled in situ inside a patient.

It would also be desirable to have a spinal implant system wherein the size of the implant may be adjusted during the procedure depending on patient anatomy without removal of the implant.

It would still further be desirable to have a minimally-invasive surgery procedure for installing an implant that could be assembled in situ inside a patient

BRIEF DESCRIPTION OF THE DRAWINGS

The features of the invention, its nature and various advantages will be more apparent from the accompanying drawings and the following detailed description of the preferred embodiments, in which:

FIG. 1A shows the first wing and shaft of an implant in accordance of one embodiment of the present invention;

FIG. 1B shows the first wing and shaft of FIG. 1A after assembly with a first spacer in accordance with one embodiment of the invention;

FIG. 1C shows the first wing and shaft of FIG. 1A after assembly with a first spacer and illustrating a second and third spacer in accordance with one embodiment of the invention;

FIG. 1D shows the first wing and shaft of FIG. 1A after assembly with a first, second and third spacer and illustrating a fourth and fifth spacer in accordance with one embodiment of the invention;

FIG. 3G shows the implant of FIG. 3F after attachment of a second wing and removal of the shaft extension in accordance with one embodiment of the invention;

DETAILED DESCRIPTION

Figure 1E:
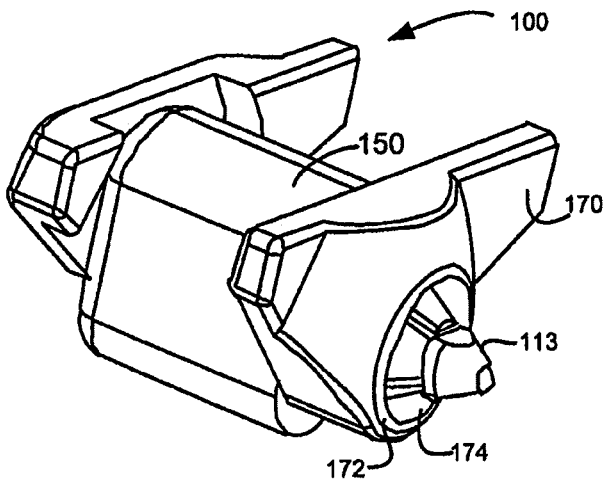
FIG. 1E shows the assembled implant of FIG. 1A after assembly with three spacers and a second wing in accordance with one embodiment of the invention.

In one embodiment, the present application is directed to a spinal implant with two plates that are connected together by a post. The implant is configured for each plate to be positioned on outer lateral sides of spinous processes with the post extending through the interspinous space. The second of the two plates includes a bore that receives the post, and that plate is movable along the length of the post to accommodate different anatomies such as for relatively wide or thin spinous processes, and selectively lockable in position. A gear nut is threaded on a distal section of the post. The gear nut includes external gear teeth that are used to drive the gear nut so as to move the second plate toward the first plate. When the plates are in their desired locations, the second plate is locked in position. The gear nut may then be removed, or may be left in place. The use of the gear nut facilitates assembly and insertion of the spinal implant.

In view of the foregoing background of the invention, it is an object of this invention to provide a spinal implant which may be assembled in situ inside the patient.

It is also an object of this invention to provide a spinal implant system wherein the size of the implant may be adjusted during the procedure depending on patient anatomy without removal of the implant.

It is still further an object of this invention to provide a minimally-invasive surgery procedure for installing an implant which may be assembled in situ inside a patient.

In accordance with the objects and background of the invention, in one embodiment, the present invention provides an implant system for implantation between adjacent spinous processes for the relief of pain associated with the spine. The implant has a series of spacers which may be inserted over a shaft located between adjacent spinous processes thus allowing the implant to be assembled in situ. The spacers limit extension motion of two adjacent spinous processes by resisting compressive forces applied to the spacer by the adjacent spinous processes. The spacer limits movement to preferably limit the collapse of the foraminal canal within which nerves are disposed. When fully assembled, the implant comprises two wings disposed on either end of the spacers. The wings resist undesired movement and maintain the location of the spacers between adjacent spinous processes. Each spacer has a tapered tissue expander to distract the opening between the spinous processes. The shaft is connected to a first wing, and after assembly of one or more spacers over the shaft, a second wing may be inserted over the shaft and locked into place. The spacers may rotate on the shaft relative to the shaft and the wings.

In one embodiment the present invention comprises, a minimally-invasive implant and implant system for alleviating discomfort associated with the spinal column. The implant includes one or more distracting spacers which are self-aligning relative to the uneven surfaces of the spinous processes. The distracting spacers are designed such that they may be inserted in a minimally-invasive manner over a shaft positioned between adjacent spinous processes. The distracting spacers may be inserted sequentially with each spacer increasing the space between the spinous processes. In this manner, the implant may be assembled in situ. The sequential distraction of the spinous process allows a surgeon to evaluate the amount of distraction incrementally and select a final implant size that best accommodates a patient's specific anatomy.

In an alternative embodiment, the implant comprises a shaft connected to a deployable wing which may be inserted between adjacent spinous processes in a collapsed (low-profile) configuration and then deployed into a locking position after passing between adjacent spinous processes. In the low-profile configuration, the implant has a roughly cylindrical shape approximating the cross-sectional shape of the shaft. This low-profile configuration allows the implant to be positioned at a surgical site by way of one or more incisions made approaching the interspinous ligament from one side of the interspinous ligament. A lead-in tissue expander is provided to pierce the interspinous ligament and proceed through the interspinous ligament into position between two adjacent spinous processes. The implant has a series of spacers which may be inserted over the shaft located after it has been located between adjacent spinous processes thus allowing the implant to be assembled in situ. In another alternative embodiment, the implant is provided with a second deployable wing which may be inserted to the implant location in a collapsed (low-profile) configuration and then deployed into a locked position.

In another embodiment the present invention comprises a minimally-invasive procedure for assembling a spinal implant in situ. A shaft attached to a first wing is first positioned between adjacent spinous processes. One or more spacers are then inserted sequentially over the shaft with each spacer increasing the space between the spinous processes. During sequential insertion of each spacer, a tapered tissue expander of each spacer expands the opening between the spinous processes incrementally. After assembly of the one or more spacers onto the shaft a second wing is inserted over the shaft and locked into place.

In an alternative procedure, the first wing connected to the shaft is a deployable wing. The shaft is positioned between the spinous processes with the wing in a low-profile configuration. In some embodiments, the implant may be positioned in its low-profile configuration at a surgical site by way of a cannula. An incision sized to receive the cannula can be made, and the cannula can be positioned at or near the surgical site. The cannula can have a cross-sectional shape generally conforming to a shape of the implant to assist in orienting the implant as desired. For example, the cannula can have a cylindrical shape generally conforming to the cylindrical shape of the shaft. After the shaft is located between adjacent spinous process, the first wing is deployed. One or more spacers are then inserted sequentially over the shaft with each spacer increasing the space between the spinous processes. After sufficient distraction is achieved, a second wing is attached or deployed.

Other implants and methods within the spirit and scope of the invention can be used to relieve pain associated with the spine and/or increase the volume of the spinal canal. Additional objects, advantages, and embodiments of the invention are set forth in part in the description which follows, and in part, will be obvious from this description, or may be learned from the practice of the invention. The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the left-most digit of a reference number identifies the drawing in which the reference number first appears.

Implant for In Situ Assembly

Referring now to FIG. 1A in which a portion of an implant 100 in accordance with one embodiment of the invention is depicted. Implant 100 includes a first wing 104 and a shaft 102 that extends from the first wing 104. First wing 104 has two surfaces 106, 108 in the same plane. Shaft 102 joins first wing 104 in the area of a surface 109 depressed below the plane of the two surfaces 106, 108. Shaft 102 is circular in cross-section for most of its length. Shaft 102 comprises a flat 105 for alignment of other components. Shaft 102 further comprises a locking groove 107 and a tissue expander 113. The surface 115 of tissue expander 113 is generally conical to allow the implant to be inserted between adjacent spinous processes. In this particular embodiment, tissue expander 113 has an expanding cross-section towards locking groove 107. Tissue expander 113 has, at its largest point, the same cross-section as shaft 102 in the region of flat 105. Tissue expander 113 is separated by detachment groove 117 from shaft extension 101. In one embodiment of this component first wing 104 and shaft 102 are formed in one piece of an implantable metal such as titanium.

In FIG. 1B a first spacer 110 is shown in position over shaft 102. As can be seen in FIG. 1B, first spacer 110 is approximately elliptical-shaped in cross-section. In some embodiments, first spacer 110 has a cross-section with a major dimension and a minor dimension, wherein the major dimension is greater than the minor dimension and, for example, less than about two times the minor dimension. In this embodiment, first spacer 110 may have a minor dimension 127 of 6 mm and a major dimension 129 of 13.7 mm. First spacer 110 can have other shapes such as circular, oval, ovoid, football-shaped, and rectangular-shaped with rounded corners and other shapes, and be within the spirit and scope of the invention. It is to be understood that first spacer 110 can be fabricated from an implantable metal such as titanium, a biocompatible polymer, or natural or synthetic bone.

It is to be understood that the cortical bone or the outer bone of the spinous processes is stronger at an anterior position adjacent to the vertebral bodies of the vertebra than at a posterior position distally located from the vertebral bodies. Also, for load bearing, it is biomechanically advantageous for the spacer to be close to the vertebral bodies. In order to facilitate this and to accommodate the anatomical form of the bone structures, as the implant is inserted between the spinous processes and/or urged toward the vertebral bodies, the first spacer 110 may rotate relative to the wings, such as first wing 104, so that first spacer 110 is optimally positioned between the spinous processes, and the first wing 104 is optimally positioned relative to the spinous processes. In this embodiment, first spacer 110 includes a tubular bore 112 which extends the length of first spacer 110. Bore 112 of first spacer 110 is received over shaft 102 of implant 100 and first spacer 110 can rotate about shaft 102. Surface 109 of first wing 104 is sized so as to allow rotation of first spacer 110.

Distal end 114 of first spacer 110 is provided with radiused surface 116. Radiused surface 116 allows first spacer 110 to be inserted over shaft 102 between adjacent spinous processes after shaft 102 has been positioned between adjacent spinous processes. Radiused surface 116 distracts the adjacent spinous processes during insertion of first spacer 110 over shaft 102. First spacer 110 is also provided with alignment holes 123, 125 which allow for additional spacers to be aligned with the first spacer during subsequent insertion.

In FIG. 1C a second spacer 120 is shown over shaft extension 101. As can be seen in FIG. 1C, second spacer 120 has the same general shape as first spacer 110. However second spacer 120 is larger than first spacer 110 and central bore 122 of second spacer 120 is designed to slidingly engage the outside of first spacer 110. Bore 122 of second spacer 120 is received over first spacer 110 of implant 100 and first spacer 110 and second spacer 120 can rotate, as one unit, about shaft 102. In one embodiment, second spacer 120 can have a minor dimension of 8 mm and a major dimension of 14.2 mm. Distal end 124 of second spacer 120 is provided with radiused surface 126. Radiused surface 126 allows second spacer 120 to be inserted over first spacer 110 between adjacent spinous processes after first spacer 110 has been positioned between adjacent spinous processes. Radiused surface 126 distracts the adjacent spinous processes during insertion of second spacer 120 in the direction of arrow 128 over first spacer 110.

Also in FIG. 1C, a third spacer 130 is shown over shaft extension 101. As can be seen in FIG. 1C, third spacer 130 has the same general shape of cross-section as second spacer 120. However third spacer 130 is larger than second spacer 120 and central bore 132 of third spacer 130 is designed to slidingly engage the outside of second spacer 120. Bore 132 of third spacer 130 is received over second spacer 120 of implant 100. First spacer 110, second spacer 120 and third spacer 130 can rotate, as one unit, about shaft 102. In one embodiment, third spacer 130 can have a minor dimension of 10 mm and a major dimension of 15.2 mm. Distal end 134 of third spacer 130 is provided with radiused surface 136. Radiused surface 136 allows third spacer 130 to be inserted over second spacer 120 between adjacent spinous processes after second spacer 120 has been positioned between adjacent spinous processes. Radiused surface 136 distracts the adjacent spinous processes during insertion of third spacer 130 in the direction of arrow 138 over second spacer 120.

In FIG. 1D, spacers 110, 120 and 130 are shown in assembled position over shaft 102 of implant 100. In FIG. 1D a fourth spacer 140 is also shown over shaft extension 101. As can be seen in FIG. 1D, fourth spacer 140 has the same general shape of cross-section as third spacer 130. However fourth spacer 140 is larger than third spacer 130 and central bore 142 of fourth spacer 140 is designed to slidingly engage the outside of third spacer 130. The bore 142 of fourth spacer 140 is received over third spacer 130 of implant 100. After assembly, first spacer 110, second spacer 120, third spacer 130, and fourth spacer 140 can rotate, as one unit, about shaft 102. In one embodiment, fourth spacer 140 can have a minor dimension of 12 mm and a major dimension of 16.3 mm. Distal end 144 of fourth spacer 140 is provided with radiused surface 146. Radiused surface 146 allows fourth spacer 140 to be inserted over third spacer 130 between adjacent spinous processes after third spacer 130 has been positioned between adjacent spinous processes. Radiused surface 146 distracts the adjacent spinous processes during insertion of fourth spacer 140 in the direction of arrow 148 over third spacer 130.

Also in FIG. 1D, a fifth spacer 150 is shown over shaft extension 101. As can be seen in FIG. 1D, fifth spacer 150 has the same general shape of cross-section as fourth spacer 140. However fifth spacer 150 is larger than fourth spacer 140 and central bore 152 of fifth spacer 150 is designed to slidingly engage the outside of fourth spacer 140. Bore 152 of fifth spacer 150 is received over fourth spacer 140 of implant 100. After assembly, first spacer 110, second spacer 120, third spacer 130, fourth spacer 140, and fifth spacer 150 can rotate, as one unit, about shaft 102. In one embodiment, fifth spacer 150 can have a minor dimension of 14 mm and a major dimension of 17.8 mm. Distal end 154 of fifth spacer 150 is provided with radiused surface 156. Radiused surface 156 allows fifth spacer 150 to be inserted over fourth spacer 140 between adjacent spinous processes after fourth spacer 140 has been positioned between adjacent spinous processes. Radiused surface 156 distracts the adjacent spinous processes during insertion of fifth spacer 150 in the direction of arrow 158 over fourth spacer 140.

Referring now to FIG. 1E, after sufficient distraction is achieved, a second wing 170 is inserted over shaft 102. Second wing 170 includes a locking ring 172 which is preferably made of PEEK. Locking ring 172 may be made out of any of the biocompatible polymers disclosed below or may be formed of titanium. In alternative embodiments, locking ring 172 may be formed in one piece with second wing 170. Locking ring 172 comprises one or more flexible fingers 174 which are deflected away from the center aperture 176 of locking ring 172 as locking ring 172 passes over tissue expander 113. When second wing 170 and locking ring 172 reach the desired locking position on shaft 102, fingers 174 fall into locking groove 107 (not shown in this view) thereby locking second wing 172 securely into place and retaining the spacers previously installed on shaft 102.

Figure 1F:
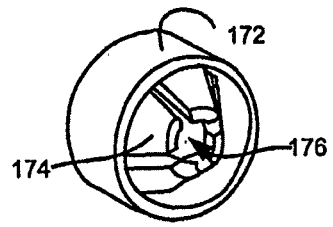
FIG. 1F shows a perspective view of the locking ring of FIG. 1E.

Referring now to FIG. 1F, a separate view of locking ring 172 is shown. As shown in FIG. 1F, in this embodiment locking ring 172 comprises four fingers 174. The four fingers 174 in their unflexed position (shown) define an aperture 176. Aperture 176, with the fingers 174 in the unflexed position, is too small to pass back over tissue expander 113, thus preventing locking ring 170 from passing back over tissue expander 113 after installation. Locking ring 172 may alternatively comprise any number of fingers sufficient to fasten locking ring 172 and second wing 170 onto shaft 102. Furthermore, locking ring 172 is only one type of fastening device which may be used to fasten second wing 170 onto shaft 102. Other types of fasteners known to those of skill in the art may be used including, for example, friction fasteners, machine screws, cotter pins and the like manufactured from biocompatible materials. Furthermore, rather than being made of one piece of titanium, first wing 104 and shaft 102 may be separate components and first wing 104 may be fastened to shaft 102 in a similar manner to second wing 170, using a locking ring, machine screws, cotter pins or the like manufactured from biocompatible materials.

Figure 1G:
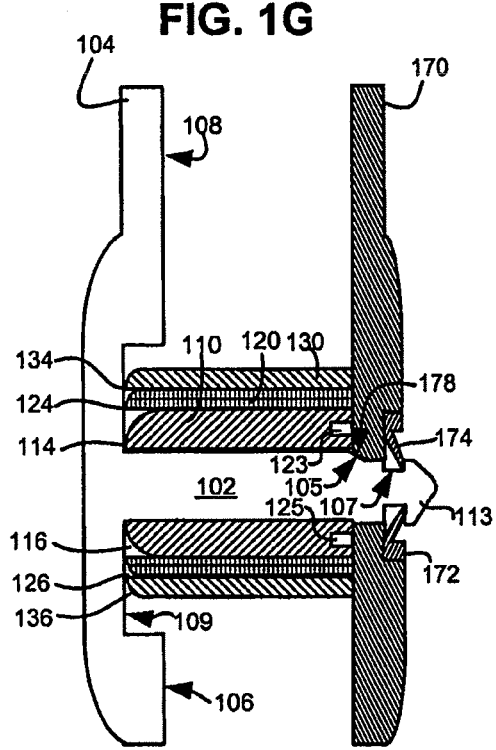
FIG. 1G shows a sectional view of the implant of FIG. 1E.

Referring now to FIG. 1G a sectional view of implant 100 is shown. As shown in FIG. 1G, first spacer 110, second spacer 120 and third spacer 130 have been assembled over shaft 102. The radiused surfaces 116, 126 and 136 at distal ends 114, 124 and 134 of first spacer 110, second spacer 120 and third spacer 130 respectively can be observed in contact with surface 109 of first wing 104. As can be observed in this sectional view, surface 109 of first wing 104 is set back from surfaces 106, 108 of first wing 104 sufficiently that no part of the radius of radiused surfaces 116, 126 and 136 cross the plane of surfaces 106, 108. This is to prevent the formation of a depression which might capture the spinous process. Furthermore, surface 109 is sized such that the spacers may rotate somewhat about shaft 102 without interfering with the raised perimeter of surface 109.

Referring again to FIG. 1G, it can be observed that second wing 170 is designed such than engagement surface 178 engages flat 105 of shaft 102 thereby preventing or limiting rotation of second wing 170 relative to shaft 102 and first wing 104. In an alternative embodiment, a gap is provided between engagement surface 178 and flat 105 thereby permitting some limited rotation of second wing 170 relative to shaft 102 and first wing 104. In yet another embodiment, shaft 102 can be made without flat 105 and second wing 170 can be formed without engagement surface 178 such that second wing 170 is free to rotate relative to shaft 102 and first wing 104.

Referring again to FIG. 1G, the interaction of fingers 174 with locking groove 107 can be observed. During installation, fingers 174 are flexed away from aperture 176 (shown in FIG. 1F) by tissue expander 113 thereby enlarging aperture 176 sufficiently to pass over tissue expander 113. However, on reaching the desired position, fingers 174 fall into locking groove 107. Fingers 174 are shaped such that, after they are positioned in locking groove 107, attempting to move locking ring 172 back over tissue expander 113 will not deflect fingers 174 away from aperture 176. Thus, once fingers 174 are located in locking groove 107, locking ring 172 and second wing 170 are fastened into place on shaft 102. After installation of second wing 170, shaft extension 101 may then be removed from shaft 102 at detachment groove 117 (not shown). The material at detachment groove 117 may either be cut, or if thin enough, may be snapped. In alternative embodiments, shaft extension 101 is releasably attached to tissue expander 113 by a threaded coupling or another releasable coupling.

Figure 1H:
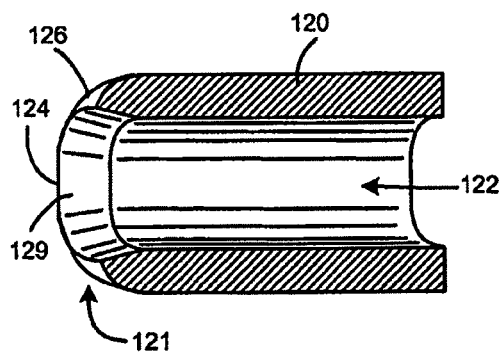
FIG. 1H shows a partially-sectional perspective view of a spacer according to one embodiment of the present invention.

FIG. 1H shows a sectional perspective view of a second spacer 120 according to one embodiment of the present invention. In this embodiment each of the spacers 110, 120, 130, 140 and 150 of implant 100 is illustrated as having a generally elliptical external shape. The spacer can have a cross-section that is elliptical, oval, ovoid, football-shaped, circular-shaped, and rectangular with rounded ends (where the cross-section has two somewhat flattened surfaces and two rounded surfaces similar to the effect of a flattened ellipse). Further, the spacers may have different cross-sectional shapes relative to each other so long as the central bore of a spacer is the same shape as the external profile of the immediately preceding spacer.

In this embodiment each of the spacers 110, 120, 130, 140 and 150 of implant 100 have been described as having a radiused surface 116, 126, 136, 146, 156 respectively for incrementally distracting the adjacent spinous processes during sequential insertion of the spacers. The radiused end of spacers 110, 120, 130, 140 and 150 of implant 100 each function as a tissue expander to push apart the adjacent spinous processes during insertion of the spacer. In other embodiments of the present invention a ramped or curved tissue expander may be provided at the distal end 114, 124, 134, 144, 154 of spacers 110, 120, 130, 140 and 150 of implant 100. Such tissue expanders provide for gradual distraction of the spinous processes during introduction of the spacer thereby facilitating the procedure. Referring again to FIG. 1H, the distal end 124 of second spacer 120 comprises a tissue expander 121. The tissue expander 121 comprises the radiused surface 126 at the distal end 124 of second spacer 120. The shape of the tissue expander 121 is designed to allow the spacer to be inserted in-site over a shaft 102 already in position between adjacent spinous processes. The radiused outer surface 126 pushes the adjacent spinous process away from one another as the spacer is introduced. Note, also, that in the embodiment of FIG. 1H, second spacer 120 has a tapered interior surface 129 leading into central bore 122. This interior taper allows for easier alignment of a spacer with a shaft or the immediately preceding spacer during the in-situ assembly of an implant. Each of spacers 110, 120, 130, 140, 150 is provided with a tissue expander at the distal end 114, 124, 134, 144, 154 respectively. Each of spacers 110, 120, 130, 140, 150 may also be provided with a tapered interior surface to facilitate alignment of the central bore of the spacer with the exterior of the shaft or the immediately preceding spacer.

At least the minor outer diameter of one or more of spacers 110, 120, 130, 140 and 150 of implant 100 is between 6 mm and 14 mm. Typically the minor outer dimension is one of 6 mm, 8 mm, 10 mm, 12 mm, and 14 mm. The different sizes enable the spacer to accommodate different sized patients and allow for incremental distraction of the spinous processes as implant 100 is assembled in situ. The major and minor dimensions of spacers 110, 120, 130, 140 and 150 of implant 100, and the number of spacers may be selected based on the particular application and the specific anatomy of the patient. A surgeon may determine that sufficient distraction has been achieved after the insertion of one or more of spacers 110, 120, 130, 140 and 150 of implant 100. In a preferred embodiment, the spacers are made from titanium. However, spacers in accordance with embodiments of the present invention can also be made from other biocompatible materials as described below.

Implant with Deployable Wing for In-Situ Assembly

Figure 2A:
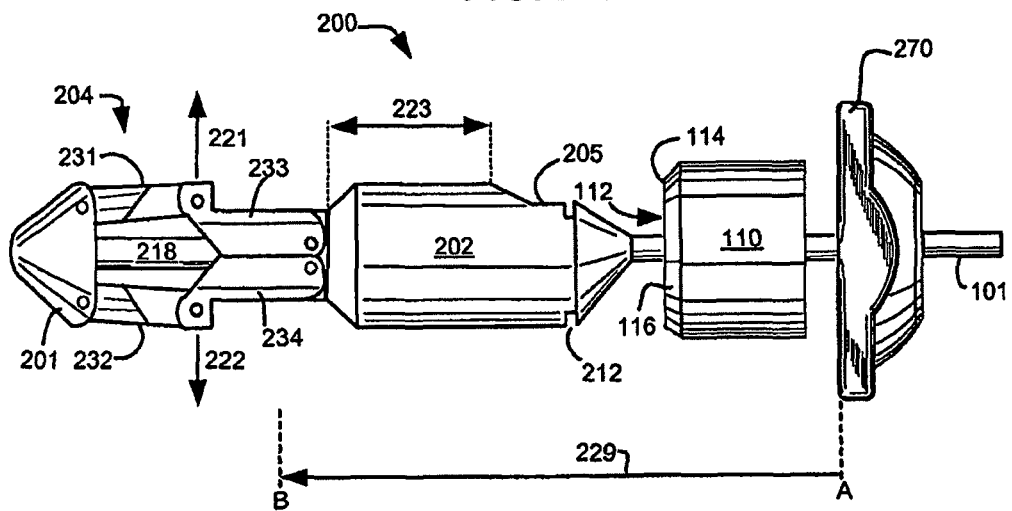
FIG. 2A shows components of an implant having a deployable wing assembly in accordance with one embodiment of the present invention.
Figure 2B:
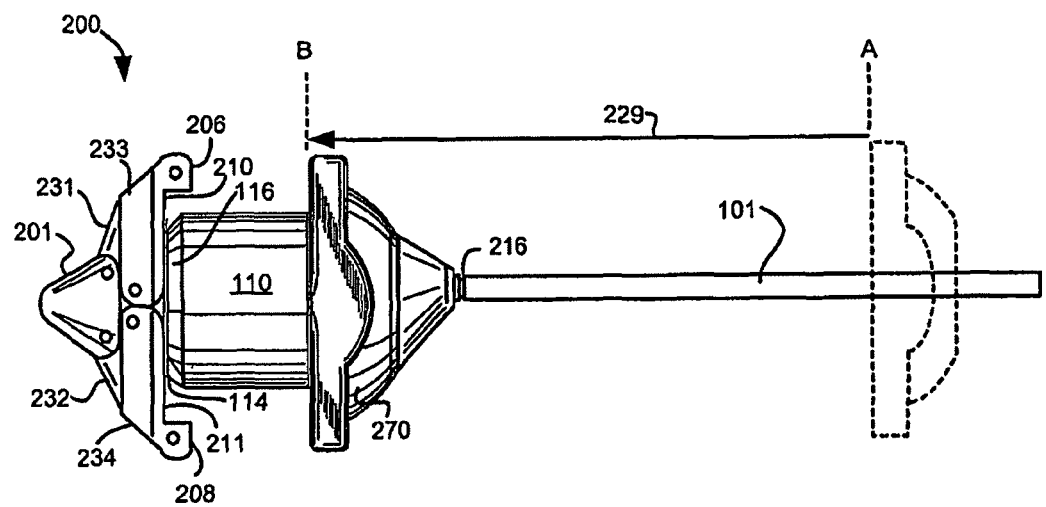
FIG. 2B shows the implant of FIG. 2A with the wing assembly deployed and the components in their assembled configuration in accordance with one embodiment of the present invention.

Referring now to FIGS. 2A-B which illustrate an implant 200 for in situ assembly in accordance with an alternative embodiment of the present invention in which implant 200 comprises a first wing which is a deployable wing. This embodiment provides a minimally-invasive procedure for assembling an implant between adjacent spinous processes for the relief of pain associated with the spine. Only a single small incision is required on one side of the spine for insertion and assembly of the implant. In the embodiment illustrated in FIGS. 2A-B, a shaft is attached to a first deployable wing which may be inserted between adjacent spinous processes in a low profile configuration and then expanded. After the wing has been deployed or expanded, from one to five spacers may then be inserted sequentially over the shaft with each spacer incrementally increasing the space between the spinous processes as with the implant 100 of FIGS. 1A-H. During introduction of each spacer a radiused surface of the spacer expands the opening between the spinous processes. A surgeon may evaluate the position of the vertebrae after each incremental distraction of the spinous processes to evaluate whether the desired effect has been achieved and determine whether an additional spacer should be inserted. After assembly of the chosen number of spacers onto the shaft, a second wing is inserted over the shaft and fastened into place retaining the spacers. Alternatively, a second deployable wing may be deployed as shown in FIG. 4F. Further details, configurations and procedures for implants comprising deployable wings may be found in U.S. patent application Ser. No. 11/389,002 entitled "Interspinous Process Implant Having Deployable Wing and Method of Implantation" to Zucherman et al. filed on Mar. 24, 2006 and assigned to the same owner as the present application which is incorporated herein by reference.

Referring now to FIG. 2A, an implant 200 having a deployable wing assembly 204 is shown in accordance with one embodiment of the invention. As shown in FIG. 2A, a first deployable wing assembly 204 is connected to shaft 202 and shaft extension 101. Shaft extension 101 in this embodiment slides through a tubular bore in the center of shaft 202. Deployable wing assembly 204 comprises lead-in tissue expander 201 which has the same cross-section as shaft 202. Lead-in tissue expander 201 is connected to shaft 202 by four segments 231, 232, 233, and 234 which are pivotally connected to each other, the lead-in tissue expander and shaft 202 such that when shaft 202 moves in the direction of arrow 220 relative to shaft extension 101, segments 231, 232, 233, 234 move in the directions shown by arrows 221 and 222. In FIG. 2A, deployable wing assembly 204 is shown in its low-profile configuration. In FIG. 2B, deployable wing assembly 204 is shown in its deployed position. Implant 200, also comprises a locking groove 212, and a flat 205 for aligning a second wing 270 and fastening second wing 270 of implant 200 to shaft 202 in the same way as with second wing 170 of implant 100 of FIGS. 1A-H.

Referring again to FIG. 2A, first spacer 110 is shown located over shaft extension 101. First spacer 110 has a tubular central bore 112 which is sized to slide over shaft 202. The distal end 114 of first spacer 110 has a radiused surface 116 for distracting the spinous processes during insertion of first spacer 110. Implant 200 also includes a second wing 270. Second wing 270 comprises an internal engagement surface 278 (not shown) for engaging flat 205 and a locking ring, as shown in FIG. 1F, for fastening second wing 270 to shaft 202. These elements are as previously discussed with respect to second wing 170 and illustrated in FIGS. 1E-H. First spacer 110 can have other shapes such as circular, oval, ovoid, football-shaped, and rectangular-shaped with rounded corners and other shapes, and be within the spirit and scope of the invention. In another embodiment, first spacer 110 has a cross-section with a major dimension and a minor dimension, wherein the major dimension is greater than the minor dimension and, for example, less than about two times the minor dimension. It is to be understood that first spacer 110 can be fabricated from an implantable metal such as titanium or a biocompatible polymer.

Implant 200 includes, in one embodiment, a second spacer 120, third spacer 130, fourth spacer 140 and fifth spacer 150 as described with respect to implant 100. As previously described, the spacers are "nested" in size such that first spacer 110 can fit inside second spacer 120 which can fit inside third spacer 130 which can fit inside fourth spacer 140 which can fit inside fifth spacer 150. First spacer 110 has a cylindrical bore that is sized to receive shaft 202 such that first spacer 110 can rotate about shaft 202. Each spacer has a length dimension which is the same as length dimension 223 of shaft 202. Each spacer has a radiused or tapered distal end which forms a tissue expander that facilitates introduction of the spacer between the spinous processes as illustrated and discussed above with respect to FIG. 1H.

Referring now to FIG. 2B where implant 200 is shown in an assembled configuration. Shaft 202 and first spacer 110 have been moved in the direction of arrow 229 relative to shaft extension 101 and tissue expander 201. Second wing 270 has been pushed in direction 229 from position A to position B. First spacer 110 is in position over shaft 202. Note that segments 233 and 234 have pivoted to a position perpendicular to shaft 202. Note also, that segments 233, 234 have a stepped configuration in which surfaces 210, 211 are set back from the plane of surfaces 206, 208. The stepped configuration means that when distal end 114 of first spacer 110 is in contact with surfaces 210 and 211, the radiused edge 116 of first spacer 110 is within a depression in the surface of segments 233, 234. Note than when second wing 270 has been urged into its locked position wherein a locking ring engages the locking groove 212, a detachment groove 216 on shaft extension 101 is revealed. The material at detachment groove 216 may be cut or snapped to remove the portion of the shaft extension protruding from second wing 270.

Procedure for In Situ Assembly of an Implant

Referring now to FIGS. 3A-G, which illustrate a procedure for assembling implant 100 in situ in accordance with one embodiment of the present invention. This embodiment provides a minimally-invasive procedure for assembling an implant at an implant location between adjacent spinous processes for the relief of pain associated with the spine. In the embodiment illustrated in FIGS. 3A-G, a shaft attached to a first wing is first positioned between adjacent spinous processes. From one to five spacers may then be inserted sequentially over the shaft with each spacer incrementally increasing the space between the spinous processes. During introduction of each spacer a radiused surface of the spacer expands the opening between the spinous processes. A surgeon may evaluate the position of the vertebrae after insertion of each spacer to evaluate whether the desired effect has been achieved and determine whether an additional spacer should be inserted. After assembly of the chosen number of spacers onto the shaft, a second wing is inserted over the shaft and fastened into place retaining the spacers and completing assembly of the implant.

For insertion of spinal implants according to one embodiment of the invention, a patient is placed, desirably in a lateral decubitus position with maximum flexion of the lumbar spine. Lateral decubitus position permits easy orientation of the main body assembly during surgery. Generally, the implant can be inserted between the spinous processes from the bottom or right side of the spinous processes to the top or left side of the spinous processes. Such orientation permits easy visualization of the implant when the spacers and second wing are to be assembled. The field is prepared for sterile surgery, and local anesthesia of the area is provided. Once the entry point is determined, local anesthetic is applied to the skin and the underlying musculature.

To insert a spinal implant in one affected vertebral area for a single level implant process, a midline incision about 1.5 inches long is made at the entry point, exposing the supraspinous ligament overlying the spinous processes at the symptomatic level. The fascia may be incised on either side of the spinous processes and supraspinous ligament. The paraspinous musculature can be elevated laterally from both sides of the midline. The supraspinous ligament is desirably preserved. The interspinous ligament may be separated to facilitate insertion of the implant.

To insert spinal implants in adjacent portions of the spine for a double level implant process, a midline incision about 3 inches long is made at the entry point, exposing the supraspinous ligament overlying the spinous processes at the appropriate segments. The fascia is incised if necessary on either side of the spinous processes and supraspinous ligament. The paraspinous musculature can be elevated laterally from both sides of the midline. A first implant 100 can be inserted at the inferior level, and a second implant 100 of the same or different size, can be inserted at the superior, adjacent level after the first implant 100 has been completely secured. If the supraspinous ligament is compromised during the procedure, it can be desirable to suture closed the excision in the ligament after insertion of the spinal implant.

Figure 3A:
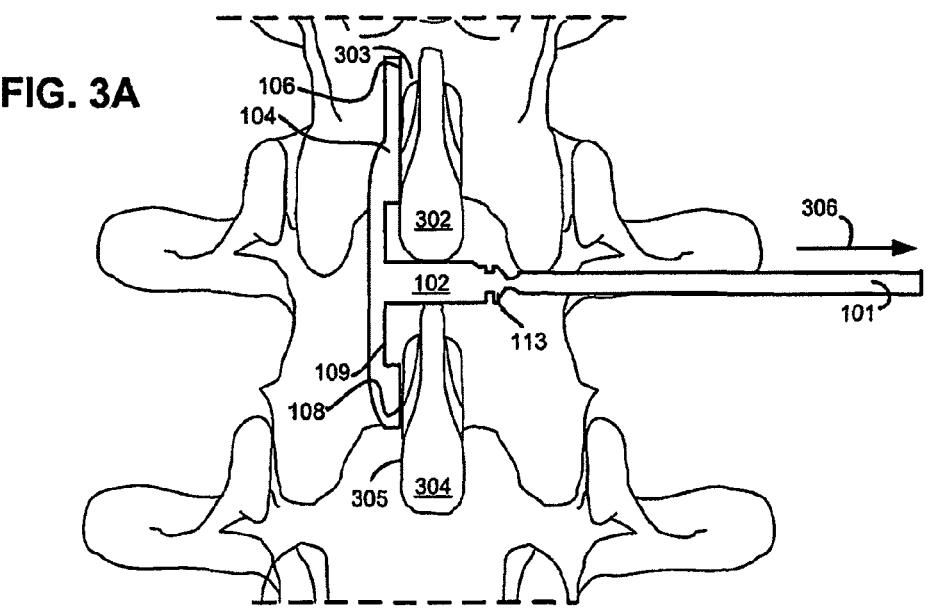
FIG. 3A shows a dorsal view of a spine with a shaft of the implant of FIGS. 1A-H positioned between adjacent spinous processes and a first wing close to the left side of the spinous processes in accordance with one embodiment of the invention.

Referring to FIG. 3A, shaft extension 101 is passed through small ports to a location between adjacent spinous processes 302, 304 in the direction shown by arrow 306. To insert shaft 102, a surgeon first pushes shaft extension 101 between the adjacent spinous process through the interspinous ligament. The surgeon then pulls on shaft 101 to pull tissue expander 113 through an opening already created between the adjacent spinous processes 302, 304. As the surgeon continues to pull on shaft extension 101, shaft 102 slides between adjacent spinous processes 302, 304 until surfaces 106, 108 of first wing 104 come into contact with the left sides 303, 305 of adjacent spinous processes 302, 304 respectively. Positioning of shaft 102 may also be aided by fluoroscopic, X-ray or other visualization technology.

Figure 3B:
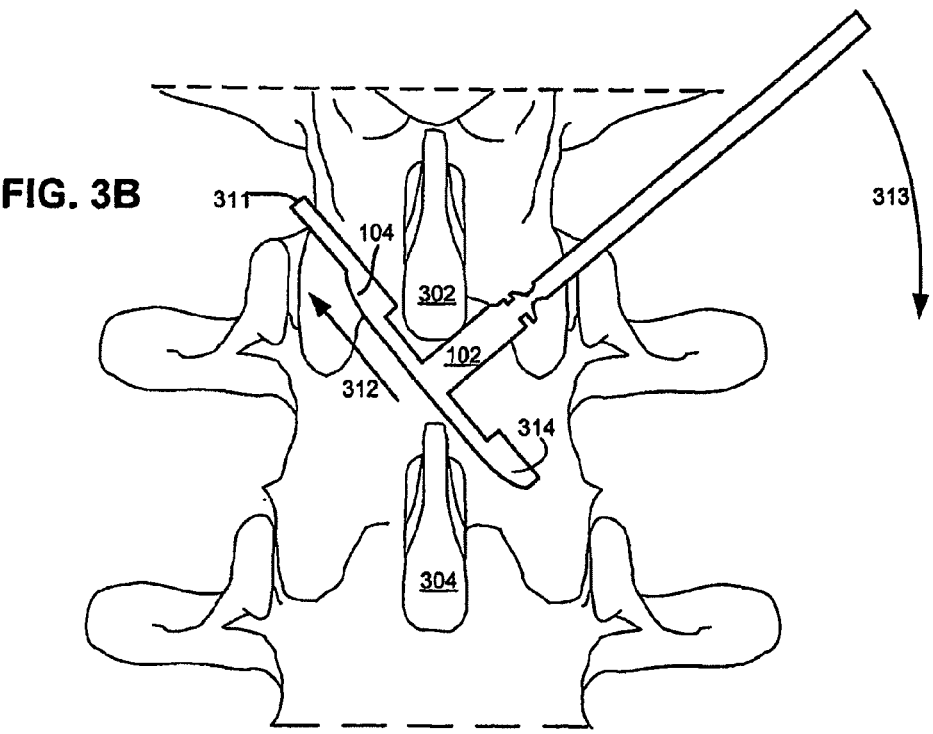
FIG. 3B shows a dorsal-view of a spine illustrating an alternative method of positioning the implant of FIGS. 1A-H between adjacent spinous processes.

In an alternative procedure, illustrated in FIG. 3B, a first end 311 of wing 104 is pushed between the adjacent spinous process through the interspinous ligament in the direction of arrow 312. The shaft extension 101 may then be drawn in the direction shown by arrow 313. As shaft extension 101 is drawn in the direction of arrow 313 the other end 314 of wing 104 passes through the interspinous ligament between the adjacent spinous processes until the wing 104 and shaft 102 are positioned as shown in FIG. 3A. This procedure has the advantage that first wing 104 and shaft 102 are deployed from the same side as the spacers and second wing. Consequently, this procedure may be performed from a single port on one side of the patient and does not require two entry ports for implantation of the implant.

Figure 3C:
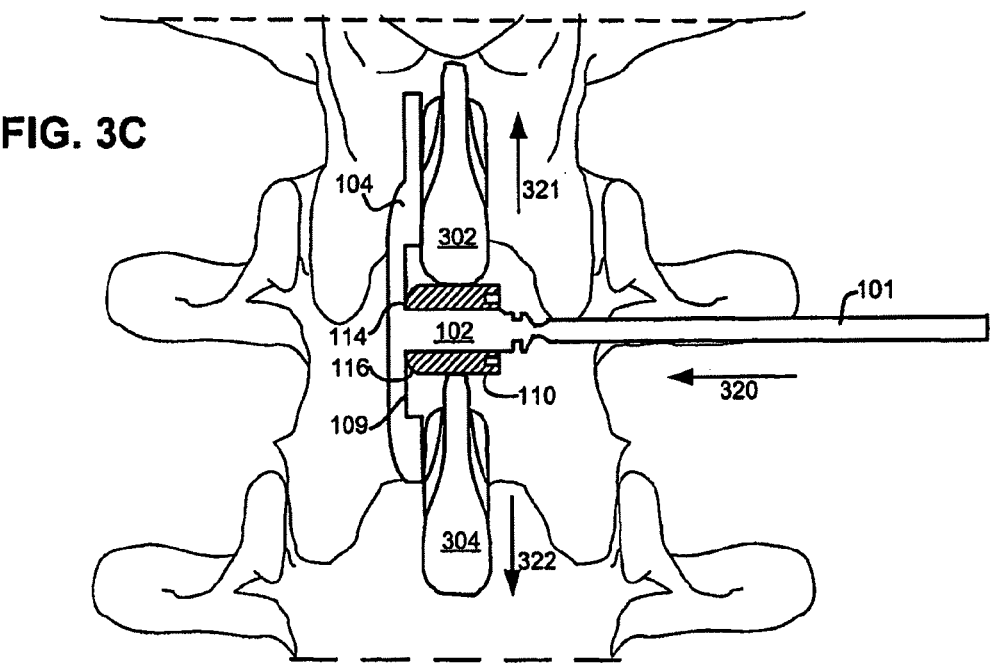
FIG. 3C shows the implant of FIG. 3A or 3B after insertion of a first spacer in accordance with one embodiment of the invention.

As shown in FIG. 3C, after the surgeon has properly located shaft 102 and first wing 104, the surgeon can insert first spacer 110 over shaft extension 101. First spacer 110 is inserted in the direction shown by arrow 320. As first spacer 110 is inserted over shaft 102, radiused surface 116 makes first contact with adjacent spinous processes 302, 304. Radiused surface 116 engages adjacent spinous processes 302, 304 and causes adjacent spinous processes 302, 304 to move apart in the directions shown by arrows 321, 322. Introduction of first spacer 110 thereby increases the distance between adjacent spinous processes 302, 304. The surgeon pushes first spacer 110 into the position shown in FIG. 3B where the distal end 114 of first spacer 110 is in contact with surface 109 of first wing 104. The surgeon may then evaluate whether the spinous processes have been sufficiently distracted and determine whether to insert additional spacers.

Figure 3D:
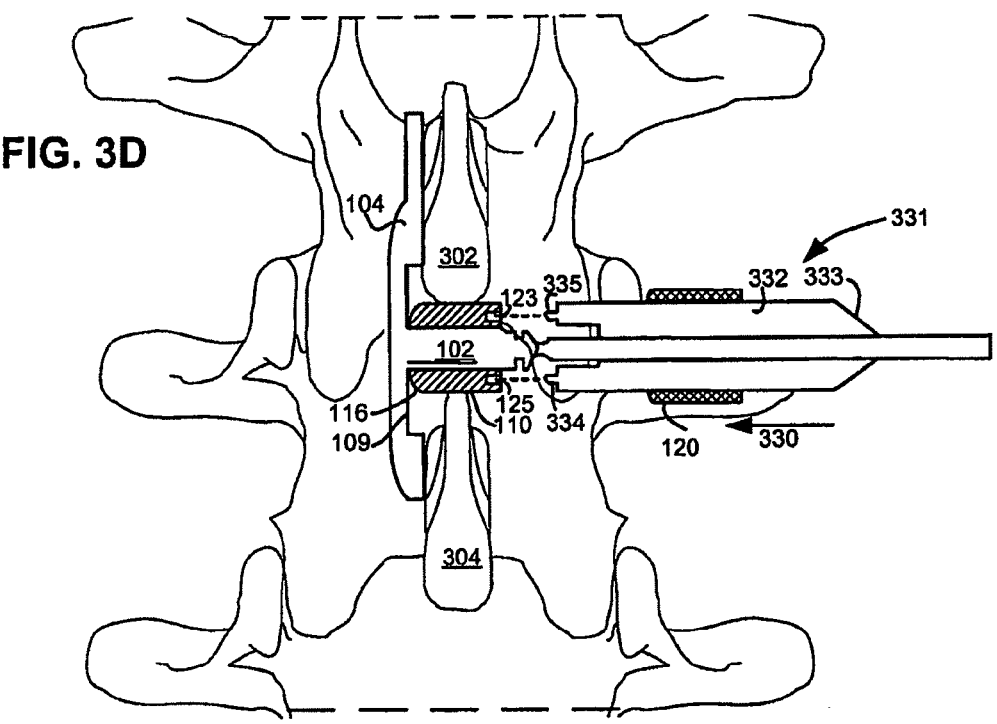
FIG. 3D shows insertion of a second spacer over the first spacer of FIG. 3C using an alignment tool according to one embodiment of the present invention.

As shown in FIG. 3D, after the surgeon has properly positioned first spacer 110 over shaft 102, second spacer 120 may be inserted in the same direction as first spacer 110. To facilitate introduction of second spacer 120 (and subsequent spacers), a mandrel in the form of an alignment tool 331 is first inserted over shaft extension 101. The main body 332 of alignment tool 331 has the same external dimensions as first spacer 110. Consequently, the main body 332 of alignment tool 331 has the same external dimensions as the interior dimensions of bore 122 of second spacer 120. Alignment tool 331 also has a central bore 334 for sliding over shaft extension 101. A tapered portion 333 of alignment tool 331 allows the surgeon to position second spacer 120 over the alignment tool outside of the patient's body and slide it towards the implant in the direction shown by arrow 330. At the distal end of alignment tool 331 are alignment pins 334, 335 which are spaced and size to engage the alignment holes 123, 125 of first spacer 110. When alignment pins 334, 335 are located in alignment holes 123, 125 the surface of alignment tool 331 is lined up with the surface of first spacer 110. Thus, second spacer 120 can be easily slipped from alignment tool 331 onto first spacer 110.

Thus, second spacer 120 is inserted in the direction shown by arrow 330 over first spacer 110 with the aid of alignment tool 331. As second spacer 120 is inserted over first spacer 110 and shaft 102, radiused surface 126 makes first contact with adjacent spinous processes 302, 304. Radiused surface 126 engages adjacent spinous processes 302, 304 and causes adjacent spinous processes 302, 304 to move apart in the directions shown by arrows 331, 332. Introduction of second spacer 120 thereby expands the distance between adjacent spinous processes 302, 304. The surgeon pushes second spacer 120 into the position shown in FIG. 3E where the distal end 124 of second spacer 120 is in contact with surface 109 of first wing 104. The surgeon may then evaluate whether the spinous processes have been sufficiently distracted and determine whether to insert additional spacers.

Figure 3E:
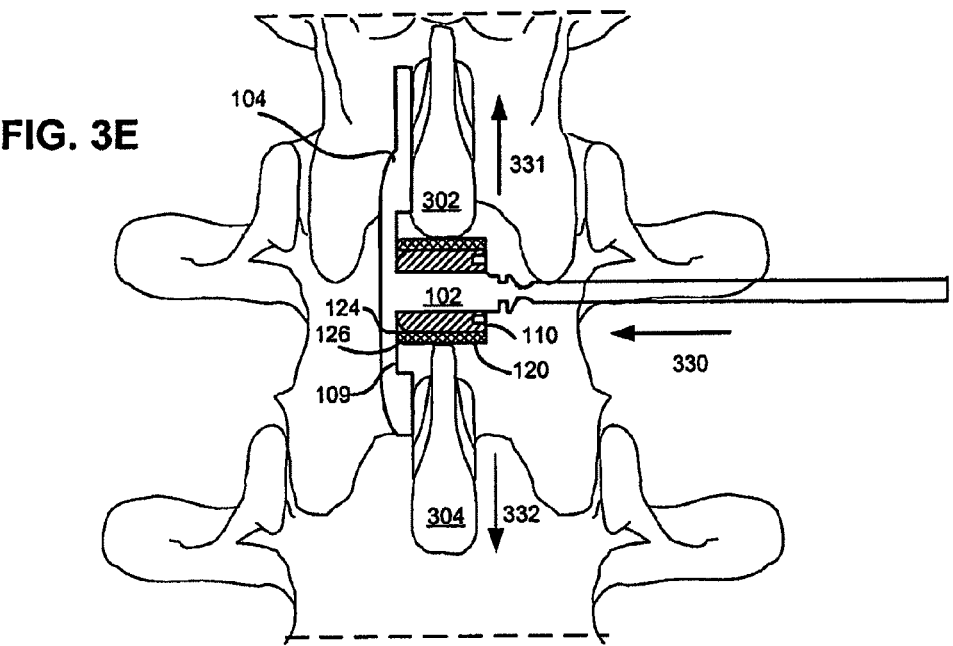
FIG. 3E shows the implant of FIG. 3C after insertion of a second spacer in accordance with one embodiment of the invention.
Figure 3F:
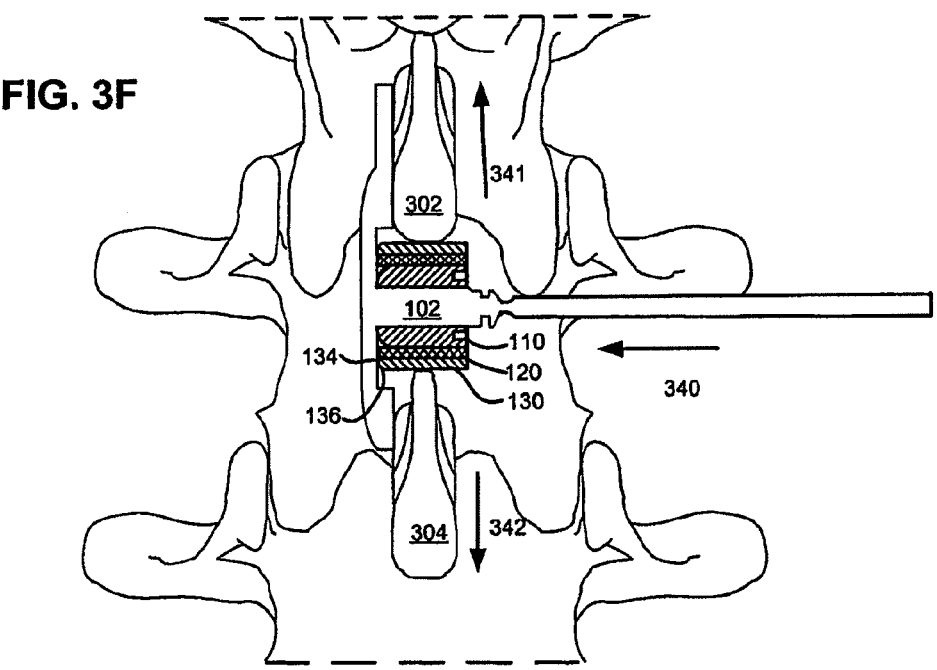
FIG. 3F shows the implant of FIG. 3E after insertion of a third spacer in accordance with one embodiment of the invention.

As shown in FIG. 3F, after the surgeon has positioned second spacer 120 over first spacer 110, third spacer 130 can be inserted over second spacer 120. Third spacer 130 is inserted in the direction shown by arrow 340. Third spacer 130 may be inserted with the aid of an alignment tool 331 which has the same external dimensions as second spacer 120. As third spacer 130 is inserted over second spacer 120, radiused surface 136 makes first contact with adjacent spinous processes 302, 304. Radiused surface 136 engages adjacent spinous processes 302, 304 and causes adjacent spinous processes 302, 304 to move apart in the directions shown by arrows 341, 342. Introduction of third spacer 130 thereby expands the distance between adjacent spinous processes 302, 304. The surgeon pushes second third spacer 130 into the position shown in FIG. 3F where the distal end 134 of third spacer 130 is in contact with surface 109 of first wing 104. The surgeon may then evaluate whether the spinous processes have been sufficiently distracted and determine whether to insert additional spacers.

After third spacer 130 is properly located over second spacer 120, the surgeon may introduce fourth spacer 140 and fifth spacer 150 in the same manner. Fourth spacer 140 and fifth spacer 150 may also be inserted with the aid of an appropriately sized alignment tool 331 which has the same external dimensions as the interior bore of the spacer being inserted. The surgeon may evaluate whether the spinous processes have been sufficiently distracted after the insertion of each spacer to determine whether to insert additional spacers. However, if sufficient distraction of spinous processes 302, 304 has been achieved, the surgeon may install second wing 170 as shown in FIG. 3G. Second wing 170 and locking ring 172 are advanced over shaft extension 101 until second wing is properly located over shaft 102 of implant 100. When second wing 170 is in the correct position, locking ring 172 engages locking groove 107, fastening locking ring 172 and second wing 170 into position on shaft 102 and retaining the spacers 110, 120, 130 installed over shaft 102. FIG. 3E depicts a dorsal view of the spine of a patient, depicting a fully-assembled implant 100 comprising, in this embodiment, first wing 104, shaft 102, spacers, 110, 120, 130 second wing 170 and locking ring 172. Depending on the anatomy of the patient, the assembled implant may comprise more or less spacers than shown. First wing 104 is shown near the left lateral surfaces of the spinous processes and second wing 170 is shown placed near the right lateral surfaces of the spinous processes. In this assembled configuration, first wing 104 and second wing 170 prevent unwanted movement of implant 100 and retain spacers 110, 120 and 130 in the correct position between spinous process 302, 304.

After installation of second wing 170, the surgeon may remove shaft extension 101 from shaft 102 at detachment groove 117 (not shown). The material at detachment groove 117 may either be cut or, if thin enough, be snapped. In alternative embodiments, shaft extension 101 is releasably attached to tissue expander 113 by a threaded coupling or another releasable coupling. After removal of the shaft extension 101, the incisions may be sutured and closed.

Procedure for In Situ Assembly of an Implant with a Deployable Wing

Figure 4A:
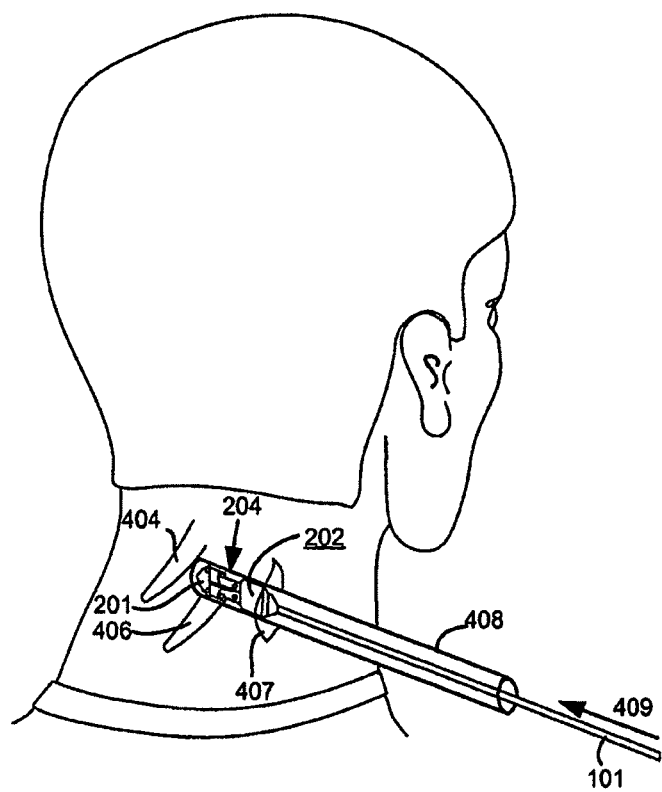
FIG. 4A shows a dorsal view of a spine illustrating introduction of the implant of FIGS. 2A-B between adjacent cervical spinous processes using a cannula in accordance with one embodiment of the invention.
Figure 4B:
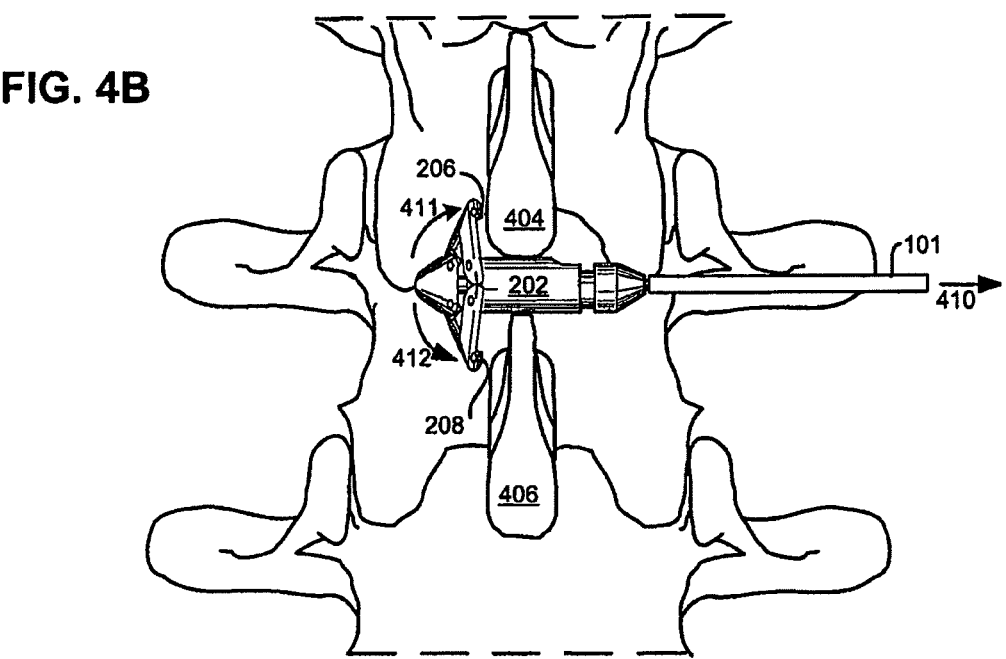
FIG. 4B shows the implant of FIG. 4A after deployment of the deployable wing.
Figure 4C:
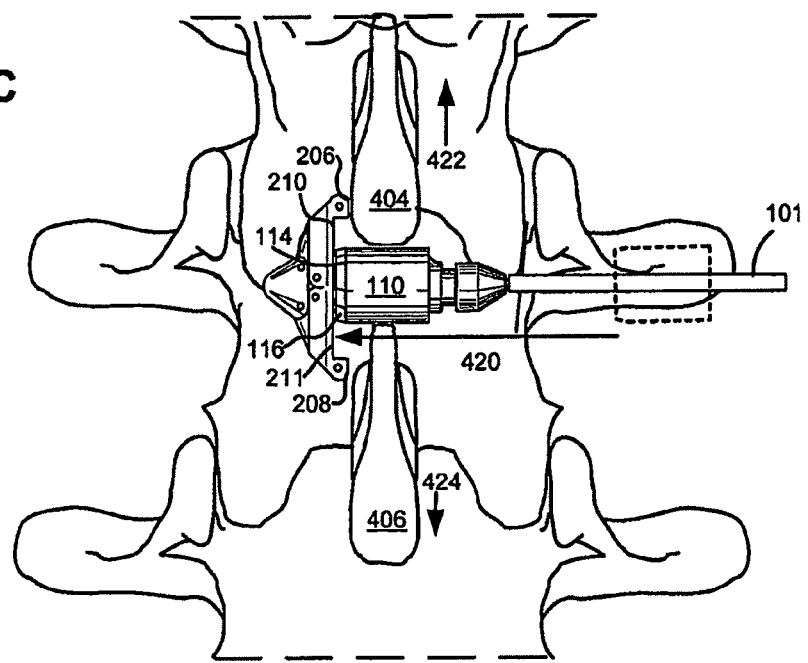
FIG. 4C shows a dorsal view of the implant of FIG. 4A after insertion of a first spacer in accordance with one embodiment of the invention.
Figure 4D:
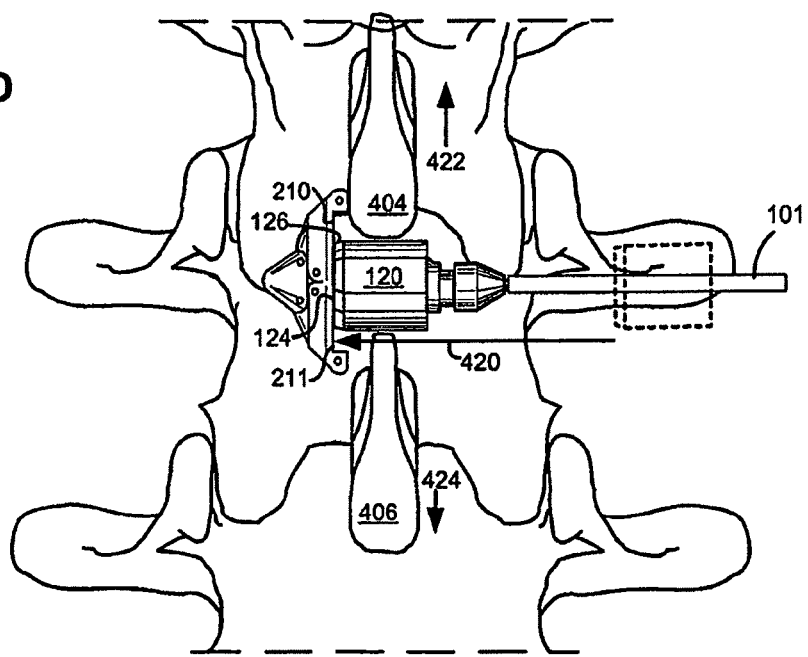
FIG. 4D shows the implant of FIG. 4A after insertion of a second spacer in accordance with one embodiment of the invention.
Figure 4E:
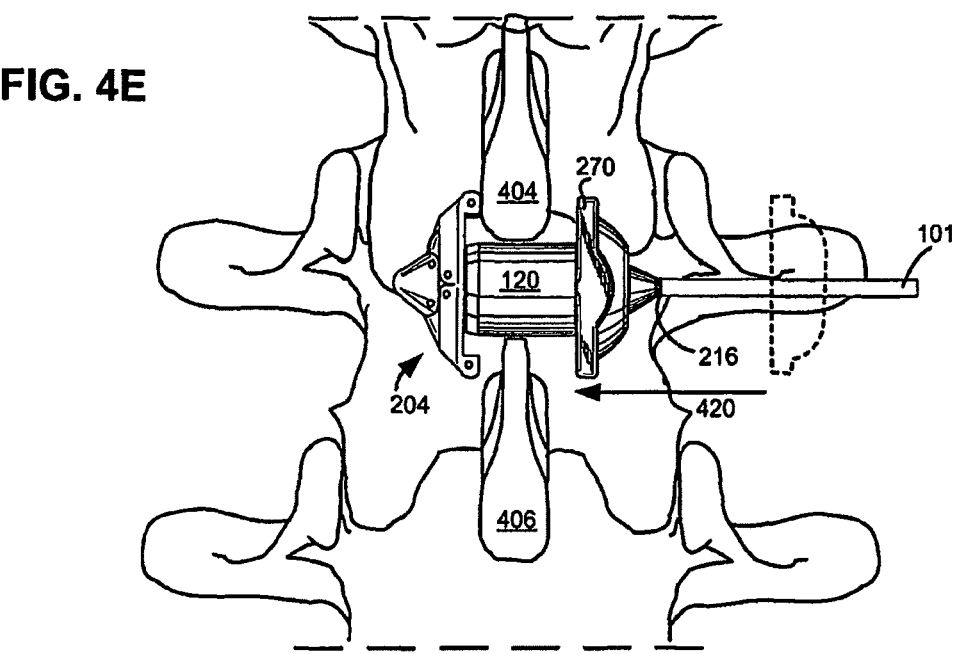
FIG. 4E shows the implant of FIG. 4A after attachment of a second wing.
Figure 4F:
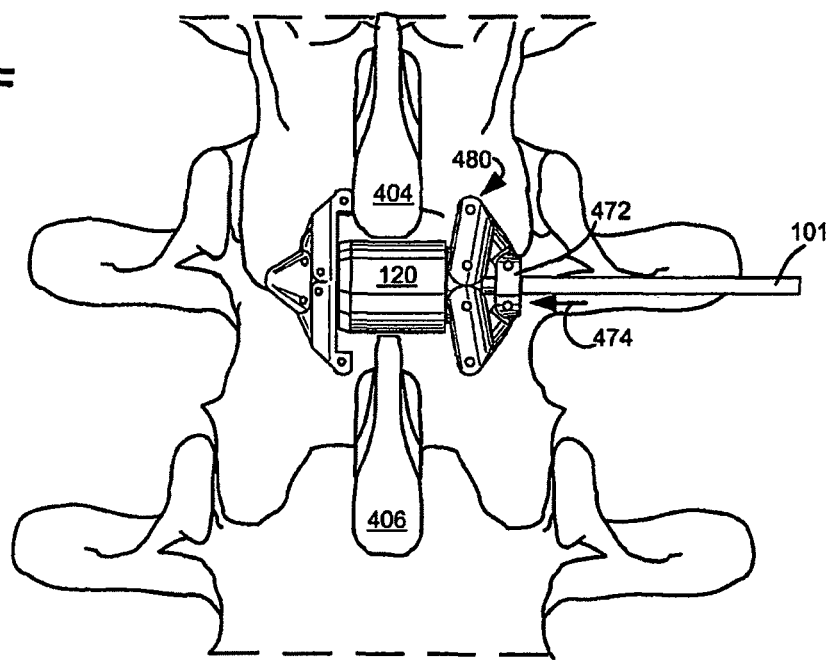
FIG. 4F shows an alternative embodiment of the implant of FIG. 4E after deployment of a second deployable wing.

Referring now to FIGS. 4A-F in which a procedure is shown for placement of implant 200 between adjacent spinous processes. Lead-in tissue expander 201 is first urged between adjacent spinous processes 404, 406 in the direction shown by arrow 402 until shaft 202 is located between the adjacent spinous processes as shown in FIG. 4A. Deployable wing assembly 204 including lead-in tissue expander 201 has, in its low profile configuration, the same cylindrical cross-section as shaft 202. To aid the introduction of lead-in tissue expander 201, a space may already have been formed between spinous processes 404, 406 using a distraction tool. Implant 200 may also be guided to the appropriate location though a cannula 408. Positioning of shaft 202 may also be aided by fluoroscopic, X-ray or other visualization technology.

As shown in FIG. 4B, after the surgeon has properly located shaft 202 between adjacent spinous processes 404, 406, first wing assembly 204 may be deployed by pulling on shaft extension 101 in the direction of arrow 410. Counter pressure is applied to shaft 202 to maintain the location of shaft 202 during deployment of wing assembly 204. Movement of shaft extension 101 in the direction of arrow 410 urges surfaces 206 and 208 of wing assembly 204 to deploy in the direction of arrows 411, 412 to positions perpendicular to shaft 202 and adjacent the lateral surfaces of the spinous processes 404, 406.

As shown in FIG. 4C, first spacer 110 is then inserted over shaft extension 101 in the direction of arrow 420 which is the same direction in which the shaft was inserted. As first spacer 110 is inserted over shaft 202, radiused surface 116 of spacer 110 makes first contact with adjacent spinous processes 404, 406. Radiused surface 116 engages adjacent spinous processes 404, 406 and causes adjacent spinous processes 404, 406 to move apart in the directions shown by arrows 422, 424. Introduction of first spacer 110 thereby expands the distance between adjacent spinous processes 404, 406. The surgeon pushes first spacer 110 into the position shown in FIG. 4C where the distal end 114 of first spacer 110 is in contact with surfaces 210, 211 of deployable wing assembly 204. Note that surfaces 210, 211 of deployable wing assembly 204 are recessed from surfaces 206, 208 of deployable wing assembly 204 in order that radiused surface 254 of first spacer 110 does not intersect the plane of surfaces 206, 208. This is to prevent spinous processes 404, 406 coming into contact with radiused surface 116 after assembly of implant 200. After insertion of first spacer 110, the surgeon may evaluate whether the spinous processes have been sufficiently distracted and determine whether to insert additional spacers.

As shown in FIG. 4D, after the surgeon has properly located first spacer 110 over shaft 202, second spacer 120 may be inserted in the same direction as first spacer 110. Second spacer 120 is inserted in the direction shown by arrow 420 over first spacer 110. Second spacer 120 has a central bore of the same cross-section as the outer surface of first spacer 110. Second spacer 120 may therefore slide over first spacer 110. Second spacer may be inserted with the alignment tool 331 shown in FIG. 3D. As second spacer 120 is inserted over first spacer 110 and shaft 202, radiused surface 126 makes first contact with adjacent spinous processes 404, 406. Radiused surface 126 engages adjacent spinous processes 404, 406 and causes adjacent spinous processes 404, 406 to move apart in the directions shown by arrows 422, 424. Introduction of second spacer 120 thereby expands the distance between adjacent spinous processes 404, 406. The surgeon pushes second spacer 120 into the position shown in FIG. 4D where the distal end 124 of second spacer 120 is in contact with surfaces 210, 211 of wing assembly 204. First spacer 110 and second spacer 120 may then rotate about shaft 202 as one unit. The surgeon may then evaluate whether the spinous processes have been sufficiently distracted and determine whether to insert additional spacers.

Additional spacers may be inserted if necessary in the same way as the second spacer and also as illustrated with respect to implant 100 in FIGS. 3A-F until the surgeon has distracted the spinous processes sufficiently to achieve the intended therapeutic result. However, if sufficient distraction of spinous processes 404, 406 has been achieved, the surgeon may install second wing 270 as shown in FIG. 4E. Second wing 270 is advanced over shaft extension 101 until second wing 270 is properly located over shaft 202 of implant 200. When second wing 270 is in the correct position a locking ring engages locking groove 212 of shaft extension 101, fastening second wing 270 into position on shaft 202 and retaining the first spacer 110, second spacer 120 and any other additional spacers as may have been installed over shaft 202. FIG. 4E depicts a dorsal view of the spine of a patient, depicting a fully-assembled implant 200 comprising, in this embodiment, first deployable wing assembly 204, shaft 202, first spacer 110, second spacer 120 and second wing 270. First wing assembly 204 is shown near the left lateral surfaces of the spinous processes and second wing 270 is shown placed near the right lateral surfaces of the spinous processes. After installation of second wing 270, the surgeon may remove shaft extension 101 from shaft 202 at detachment groove 216. The material at detachment groove 216 may either be cut or, if thin enough, be snapped. In alternative embodiments, shaft extension 101 comprises a releasable coupling such as a threaded coupling or another releasable coupling. After removal of the shaft extension 101, the incisions may be sutured and closed.

FIG. 4F illustrates an alternative embodiment of implant 200 in which a second deployable wing assembly 480 is used in place of second wing 270. Deployable wing assembly 280 may be attached to shaft 202. If second deployable wing assembly is attached to shaft 202, it must have the same tubular cross-section as shaft 202 in order to allow, first spacer 110 to pass over it in its low profile configuration. After assembly of all required spacers, the wing is deployed into its operating position as shown in FIG. 4F by pushing rear linkage 472 of second deployable wing assembly 470 in the direction of arrow 474. Rear linkage 472 may be provided with a locking ring as previously illustrated which engages a locking groove 202 in shaft extension 101 to prevent the second deployable wing from collapsing after it has been deployed. Alternatively, the second deployable wing may be a separate unit from shaft 202 which may be introduced in a low-profile configuration over shaft 202 after assembly of all required spacers.

Figure 5:
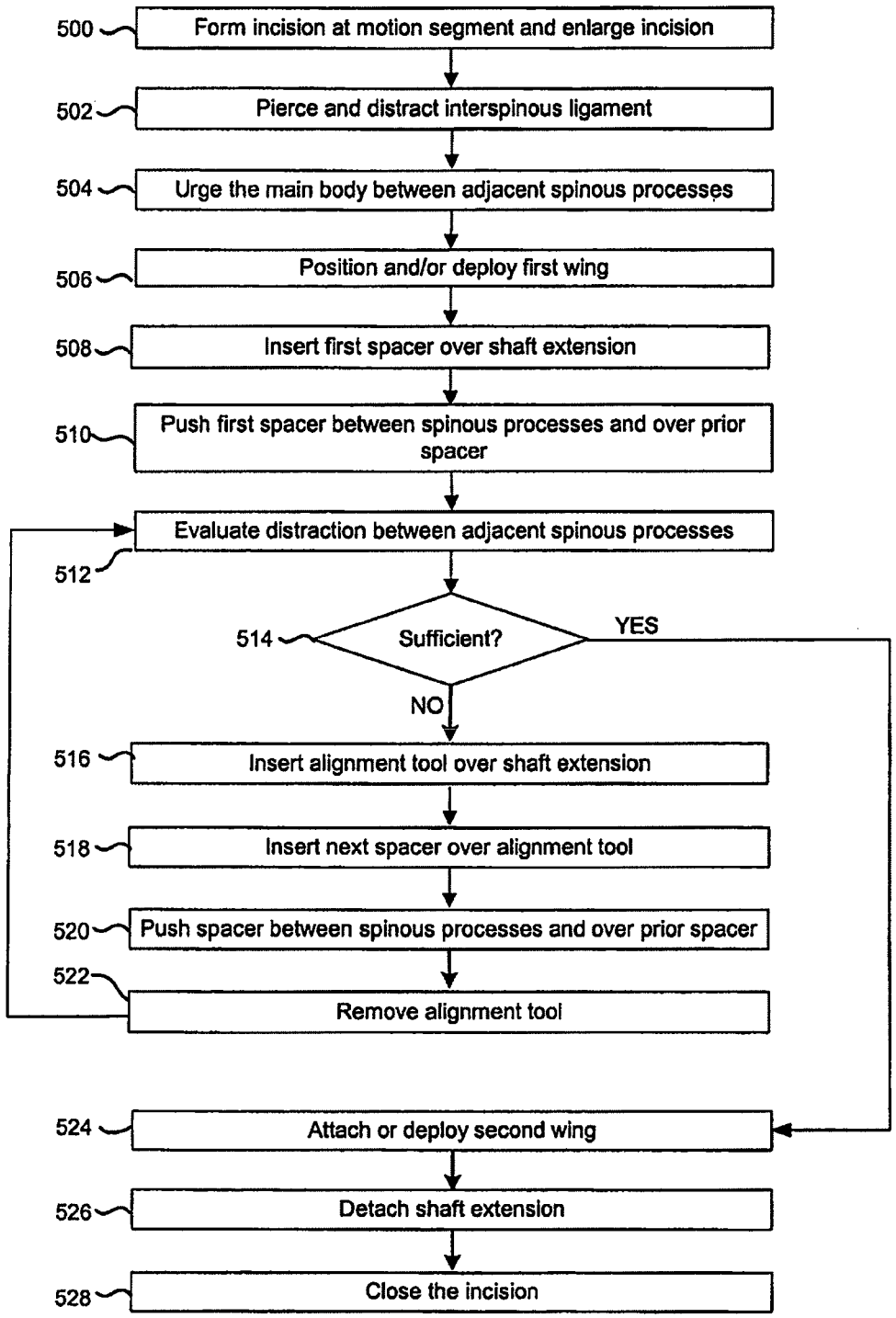
FIG. 5 is a flow diagram illustrating the steps of a procedure for implantation of an implant according to embodiments of the invention.

FIG. 5 illustrates a summary of the steps for implanting and assembling in situ an implant in accordance with the present invention. At step 500, the physician makes an incision at the motion segment to be treated and enlarges the incision sufficiently to visualize the motion segment and perform the procedure. At step 502, the physician pierces the interspinous ligament and distracts apart the spinous processes using a tissue expander of the implant or a separate tissue expander instrument. At step 504, the physician urges the main body of the implant between adjacent spinous processes to position the shaft between the spinous processes and through the interspinous ligament. At step 506, the physician positions and/or deploys the first wing. At step 508 the physician inserts the first spacer over the shaft extension 101. At step 510, the physician urges the first spacer over the shaft of the implant and between the adjacent spinous processes thereby distracting apart the adjacent spinous processes. An alignment tool is generally not required for insertion of the first spacer as the first spacer has a cylindrical bore and can slide over the shaft at whatever angle it is rotated about the longitudinal axis of the shaft. After insertion of the first spacer, the physician evaluates the amount of space created between the adjacent spinous processes by the first spacer. The physician can make this evaluation by direct visual inspection or using fluoroscopic or other imaging technologies.

At step 514, if the first spacer has not created sufficient distraction between the adjacent spinous process to alleviate the problems at that motion segment, the physician proceeds with steps 516 to 522 in which another spacer is inserted. Where an additional spacer is required, at step 516 the physician inserts an alignment tool over the shaft extension and engages the first spacer with it. At step 518 the physician inserts the next spacer over the alignment tool. The alignment tool acts as a mandrel for the next spacer and allows it to be inserted over the prior spacer at step 520. The additional spacer further distracts the adjacent spinous process as the spacer is urged over the shaft. After the additional spacer is in position over the shaft, the physician removes the alignment tool at step 522. The physician can then return to step 512 to evaluate the distraction between the adjacent spinous processes.

At step 514, if sufficient distraction has been achieved, the physician proceeds to step 524 to complete the procedure. At step 524, the physician attaches and/or deploys the second wing. When the second wing is detached and deployed, the locking ring or a similar fastener locks the second wing into place thereby retaining any spacers installed over the shaft. At step 526, the physician detaches the shaft extension by snapping, cutting or decoupling the shaft extension from the implant. At step 528, the physician closes the entry port or ports using standard surgical procedures.

Materials for Use in Implants of the Present Invention

In some embodiments, the implant can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. As an alternative to metal, the spacers of the present invention may be formed from natural or synthetic bone material.

Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryl ester ketones which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
|---|---|
| Density | 1.3 g/cc |
| Rockwell M | 99 |
| Rockwell R | 116 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketone-ketone (PEKEKK), polyether-etherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02148 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate7, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

An implant system for implantation between adjacent spinous processes for the relief of pain associated with the spine is described hereinabove. The implant has a series of spacers which may be inserted over a shaft located between adjacent spinous processes thus allowing the implant to be assembled in situ. The spacers may rotate on the shaft relative to the wings. To minimize trauma to the patient, each spacer has a tapered tissue expander to distract the opening between the spinous processes during assembly. The shaft is connected to a wing which may be a deployable wing. After assembly of one or more spacers over the shaft, a second wing or deployable wing may be inserted over the shaft and locked into place. An implant system for implantation between adjacent spinous processes for the relief of pain associated with the spine. The implant has a series of spacers which may be inserted over a shaft located between adjacent spinous processes thus allowing the implant to be assembled in situ. The spacers may rotate on the shaft relative to the wings. To minimize trauma to the patient, each spacer has a tapered tissue expander to distract the opening between the spinous processes during assembly. The shaft is connected to a wing which may be a deployable wing. After assembly of one or more spacers over the shaft, a second wing or deployable wing may be inserted over the shaft and locked into place.

The foregoing descriptions of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An implant to be assembled in situ for maintaining a space between adjacent spinous processes, the implant comprising:
    a first wing attached to a shaft;
    a first spacer which can slide onto the shaft after the shaft has been positioned between adjacent spinous processes wherein the first spacer comprises a first tissue expander which can distract the adjacent spinous processes when the first spacer is slid onto the shaft;
    a second wing; and
    a fastening device which engages the shaft and the second wing to secure the second wing to the shaft, the fastening device includes a locking ring and one or more flexible fingers configured to engage a locking groove disposed on the shaft.

2. The implant of claim 1 further comprising a second spacer which can slide over the first spacer after the first spacer has been positioned between adjacent spinous processes wherein the second spacer comprises a second tissue expander which can distract the adjacent spinous processes when the second spacer is slid over the first spacer.

3. The implant of claim 2 further comprising a third spacer which can slide over the second spacer after the second spacer has been positioned between adjacent spinous processes and wherein the third spacer comprises a third tissue expander which can distract the adjacent spinous processes when the third spacer is slid over the second spacer.

4. The implant of claim 3 further comprising a fourth spacer which can slide over the third spacer after the third spacer has been positioned between adjacent spinous processes and wherein the second spacer comprises a second tissue expander which can distract the adjacent spinous processes when the fourth spacer is slid over the third spacer.

5. The implant of claim 4 further comprising a fifth spacer which can slide over the fourth spacer after the fourth spacer has been positioned between adjacent spinous processes and wherein the fifth spacer comprises a fifth tissue expander which can distract the adjacent spinous processes when the fifth spacer is slid over the fourth spacer.

6. The implant of claim 1 wherein the first wing comprises a depression which can receive the first tissue expander after the first tissue expander has passed between the adjacent spinous processes to reduce subsequent contact between the adjacent spinous processes and the first tissue expander.

7. The implant of claim 1 wherein the shaft has a central longitudinal axis and maximum shaft diameter perpendicular to the longitudinal axis and wherein one of the first wing and the second wing has a maximum wing diameter perpendicular to the longitudinal axis of the shaft which, in a first configuration, is less than or approximately equal to the maximum shaft diameter, and which, in a second configuration, is greater than the maximum shaft diameter.

8. A method for in situ assembly of an implant for maintaining a space between adjacent spinous processes for a therapeutic purpose, wherein the implant comprises a shaft, a first wing, a second wing and at least one spacer and wherein the method comprises:
   A) positioning the shaft between adjacent spinous processes;
   B) distracting the adjacent spinous processes by positioning a first spacer over the shaft while the shaft is positioned between adjacent spinous processes;
   C) fastening with a fastening a device the second wing onto the shaft after the first spacer has been positioned over the shaft and while the shaft and first spacer are positioned between adjacent spinous processes thereby retaining the first spacer over the shaft and between the spinous processes, wherein the fastening device includes a locking ring and one or more flexible fingers configured to engage a locking groove disposed on the shaft.

9. The method of claim 8 wherein step B) comprises further distracting the adjacent spinous processes by positioning a second spacer over the first spacer while the first spacer is positioned between adjacent spinous processes.

10. The method of claim 9 wherein step B) comprises further distracting the adjacent spinous processes by positioning a third spacer over the first spacer while the second spacer is positioned between adjacent spinous processes.

11. The method of claim 10 wherein step B) comprises further distracting the adjacent spinous processes by positioning a fourth spacer over the third spacer while the third spacer is positioned between adjacent spinous processes.

12. The method of claim 11 wherein step B) comprises further distracting the adjacent spinous processes by positioning a fifth spacer over the fourth spacer while the fourth spacer is positioned between adjacent spinous processes.

13. The method of claim 8 wherein step B) comprises: B) distracting the adjacent spinous processes by positioning a first spacer over the shaft while the shaft is positioned between adjacent spinous processes; B1) incrementally distracting the adjacent spinous processes by sequentially inserting additional spacers over the shaft and all previously inserted spacers.

14. The method of claim 13 wherein step B) comprises: B) distracting the adjacent spinous processes by positioning a first spacer over the shaft while the shaft is positioned between adjacent spinous processes; B1) incrementally distracting the adjacent spinous processes by sequentially inserting additional spacers over the shaft and all previously inserted spacers; B2) evaluating the space between the adjacent spinous processes after inserting each additional spacer.

15. The method of claim 8 wherein step B) comprises: B) distracting the adjacent spinous processes by positioning a first spacer over the shaft while the shaft is positioned between adjacent spinous processes; B1) evaluating the space between the adjacent spinous processes; B2) incrementally distracting the adjacent spinous processes by inserting an additional spacer over the shaft and all previously inserted spacers; and wherein steps B1 and B2 are repeated until the space between the adjacent spinous processes is determined to be adequate for the therapeutic purpose.

16. The method of claim 8 wherein the shaft has a central longitudinal axis and maximum shaft diameter perpendicular to the longitudinal axis and wherein the first wing has a maximum wing diameter perpendicular to the longitudinal axis of the shaft which, in a first configuration, is less than or approximately equal to the maximum shaft diameter, and which, in a second configuration, is greater than the maximum shaft diameter, wherein step A comprises: A1) pushing the first wing in the first configuration between adjacent spinous processes until the first wing is distal to the adjacent spinous processes; A2) causing the wing to transition from the first configuration to the second configuration; and A3) positioning the shaft between adjacent spinous processes.

17. An implant to be assembled in situ for maintaining a space between adjacent spinous processes, the implant comprising:
   a shaft insertable laterally between the spinous processes along an axis of the shaft;
   a first wing attached to the shaft, the first wing extending from the shaft so as to inhibit movement of the shaft from the between the spinous processes;
   a first spacer having an opening, the opening slidable onto and over the shaft after the shaft has been positioned between the adjacent spinous processes, the first spacer having a first tissue expander extending from a spacer body, the tissue expander tapering axially so as to distract the adjacent spinous processes when the first spacer is slid onto the shaft, the spacer body configured to maintain distraction of the adjacent spinous processes;
   a second, third, fourth and fifth spacer configured for incremental distraction of the adjacent spinous processes by sequentially inserting the first, second, third, fourth and fifth spacers over the shaft and all previously inserted spacers;
   a second wing securable to the shaft so as to restrain the spacer between the wings while the wings inhibit movement of the shaft from between the spinous processes. the wings inhibit movement of the shaft from between the spinous processes.

* * * * *